United States Patent
Shia et al.

(10) Patent No.: US 6,706,739 B2
(45) Date of Patent: Mar. 16, 2004

(54) IMIDAZOLIDINONE COMPOUNDS

(75) Inventors: Kak-Shan Shia, Taipei (TW); Shin-Ru Shih, Taoyuan (TW); Chung-Ming Chang, Taipei (TW); Jyh-Haur Chern, Taipei (TW); Wen-Tai Li, Hsinchu (TW); Shu-Jen Chen, Taipei (TW); Ming-Chu Hsu, Glendora, CA (US)

(73) Assignee: National Health Research Institute, Taipei (TW)

( * ) Notice: Subject to any disclaimer, the term of this patent is extended or adjusted under 35 U.S.C. 154(b) by 51 days.

(21) Appl. No.: 10/191,941

(22) Filed: Jul. 9, 2002

(65) Prior Publication Data
US 2003/0087936 A1 May 8, 2003

Related U.S. Application Data
(60) Provisional application No. 60/313,878, filed on Aug. 21, 2001.

(51) Int. Cl.[7] .................. A61K 31/44; A61K 31/415; C07D 401/14; C07D 233/02; C07D 233/30
(52) U.S. Cl. .................. 514/341; 514/392; 546/274.1; 548/311.1; 548/323.5
(58) Field of Search ................... 514/341, 392; 546/274.1; 548/311.1, 323.5

(56) References Cited

FOREIGN PATENT DOCUMENTS

| WO | WO 96/31485 | * 10/1996 |
|---|---|---|
| WO | WO 02/14354 | * 2/2002 |

* cited by examiner

*Primary Examiner*—D. Margaret Seaman
(74) *Attorney, Agent, or Firm*—Fish & Richardson P.C.

(57) ABSTRACT

A compound having the formula:

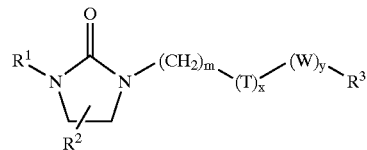

in which $R^1$, $R^2$, $R^3$, T, W, m, x, and y are defined as in the specification. Also disclosed is a method of treating enterovirus infection by using a compound described above.

38 Claims, No Drawings

IMIDAZOLIDINONE COMPOUNDS

RELATED APPLICATION

Pursuant to 35 U.S.C. § 119(e), this application claims the benefit of prior U.S. provisional application 60/313,878, filed Aug. 21, 2001.

BACKGROUND

The Picornaviridae family includes nearly 70 distinct serotypes of enteroviruses (EVs). Clinical manifestations of enterovirus infection range from mild "summer cold" to neurological and cardiovascular disorders.

An enterovirus consists of a simple virus capsid and a single strand of positive sense RNA. The capsid contains four proteins, VP1 to VP4. Variations within capsid proteins VP1 to VP3 are responsible for antigenic diversity among the enteroviruses, with neutralization sites most densely clustered on VP1 (Rueckert, *Virology*, Lippincott-Raven, New York, 1990, 507). Replication of RNA viruses is directed by viral RNA polymerase of relatively low fidelity that have an error frequency of $10^{-3}$ to $10^{-4}$ misincorporated nucleotides per round of replication (Holland et al., *Science*, 1982, 215:1576–1585; Ward et al., *J. Virol.*, 1988, 62:558–562; and La Torre et al., *J. Virol.*, 1990, 64:664–671). In other words, replication of an enteroviruses genome consisting of about 7500 nucleotides results in a population molecules having on average at least one mutation. Moreover, recombination occurs at a very high frequency in the picornaviruse family (McCahon, *Arch. Virol.*, 1981, 69:1–23).

There is a need to develop compounds which are effective in treating infection by genetically heterogeneous enteroviruses.

SUMMARY

One aspect of the present invention relates to a compound having the generic formula:

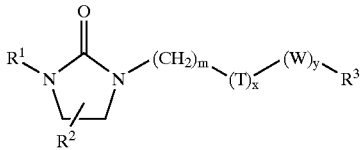

Referring to the formula, each of $R^1$ and $R^3$, independently, is $C_{6-12}$ aryl, $C_{6-12}$ aralkyl, or heteroaryl, optionally substituted with one or more halogen, $-OR^4$, $C_{1-4}$ alkyl, $C_{1-4}$ haloalkyl, $C_{1-4}$ alkyl-$OR^4$, $-CN$, $-C(O)R^4$, $-SR^4$, $-S(O)R^4$, $-S(O)_2R^4$, $-NR^4R^5$, $-C(O)OR^4$, $-C(O)NR^4R^5$, $-NO_2$, $-O(O)CR^4$, $-NR^4(O)CR^5$, $-NR^4C(O)OR^5$, $-NR^4C(O)NR^5R^6$, or $R^7$, provided that if $R^1$ is heteroaryl, the heteroaryl forms a C—N bond with the imidazolidinone ring. $R^2$ is H, $C_{1-5}$ alkyl, $C_{1-5}$ haloalkyl, $C_{6-12}$ aryl, $C_{6-12}$ aralkyl, or heteroaryl, optionally substituted (e.g., mono- or di-substituted) with halogen, $-OR^4$, $C_{1-4}$ alkyl, $C_{1-4}$ haloalkyl, $C_{1-4}$ alkyl-$OR^4$, $-CN$, $-C(O)R^4$, $-SR^4$, $-S(O)R^4$, $-S(O)_2R^4$, $-NR^4R^5$, $-C(O)OR^4$, $-C(O)NR^4R^5$, $-NO_2$, $-O(O)CR^4$, $-NR^4(O)CR^5$, $-NR^4C(O)OR^5$, or $-NR^4C(O)NR^5R^6$. Each of $R^4$, $R^5$, and $R^6$, independently, is H or $C_{1-4}$ alkyl. $R^7$ is $C_{6-12}$ aryl, $C_{6-12}$ aralkyl, or heteroaryl, optionally substituted with halogen, $C_{1-4}$ alkyl, $C_{1-4}$ haloalkyl, $-OR^4$, $-NO_2$, $-C(O)OR^4$, $-CN$, $-NR^4R^5$, or $NR^4C(O)OR^5$. T is NH or O; W is $-CH_2-O-$, $-(CH_2)_2-O-$, $-(CH_2)_3-O-$, or $-(CH_2)_4-O-$; m is 4, 5, 6, 7 or 8; and each of x and y, independently, is 0 or 1, provided that at least one of x and y is 1.

The term "halogen" refers to fluorine, chlorine, bromine or iodine. The term "alkyl" refers to a hydrocarbon chain that may be a straight chain or branched chain, containing the indicated number of carbon atoms. For example, a $C_4$ alkyl has 4 carbon atoms. The term "haloalkyl" refers to a straight-chain or branched hydrocarbon chain in which at least one hydrogen is replaced with halogen (e.g., $-C(CH_3)_2CH_2Cl$ or $-CF_3$). The term "aryl" refers to a 6 to 12-carbon monocyclic or multicyclic aromatic system wherein up to 4 atoms of each ring may be substituted by a substituent. Examples of aryl groups include but are not limited to phenyl and naphthyl. The term "aralkyl" refers to alkyl substituted with aryl. The term "heteroaryl" refers to an aromatic 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic (each heteroatom being O, N, or S). Examples of heteroaryl groups include but are not limited to pyridyl, furyl, imidazolyl, benzimidazolyl, pyrimidinyl, quinolinyl, indolyl, and thiazolyl. The aryl or heteroaryl group can be connected to other moieties at one of more ring atoms that are available. For instance, a pyridyl can be connected at its 2-, 3- or 4-position with the 1-N atom of the imidazolidinonyl group.

Referring to the above formula, one subset of the compounds are featured by that each of $R^1$ and $R^3$, independently, is $C_{6-12}$ aryl, $C_{6-12}$ aralkyl, or heteroaryl, optionally substituted with halogen, $-OR^4$, $C_{1-4}$ alkyl, $C_{1-4}$ haloalkyl, $C_{1-4}$ alkyl-$OR^4$, $-CN$, $-SR^4$, $-NR^4R^5$, $-NR^4C(O)NR^5R^6$, or $R^7$; and $R^7$ is $C_{6-12}$ aryl or heteroaryl, optionally substituted with $C_{1-4}$ haloalkyl, halogen, $-OR^4$, or $-NO_2$. These compounds include those in which each of $R^1$ and $R^3$, independently, can be pyridinyl, phenyl, or thiazolyl, optionally substituted with halogen, $-OR^4$, $C_{1-4}$ alkyl, $C_{1-4}$ alkyl-$OR^4$, $-CN$, $-SR^4$, $-NR^4R^5$, $-NR^4C(O)NR^5R^6$, or $R^7$, wherein $R^7$ is $C_{6-12}$ aryl or heteroaryl, optionally substituted with $C_{1-4}$ haloalkyl, halogen, $-OR^4$, or $-NO_2$; those in which $R^2$ can be H, $C_{1-5}$ alkyl, $C_{1-5}$ haloalkyl, $C_{6-12}$ aryl, $C_{6-12}$ aralkyl, or heteroaryl, optionally substituted with halogen, $-OR^4$, $C_{1-4}$ alkyl, $C_{1-4}$ haloalkyl, $C_{1-4}$ alkyl-$OR^4$, $-CN$, $-SR^4$, $-NR^4R^5$, or $-C(O)NR^4R^5$; and those in which x is 1 and T is O.

Another subset of the compounds are featured by that $R^2$ is H, $C_{1-5}$ alkyl, $C_{6-12}$ aryl, $C_{6-12}$ aralkyl, or heteroaryl, optionally substituted with halogen, $-OR^4$, $C_{1-4}$ alkyl, $C_{1-4}$ haloalkyl, $C_{1-4}$ alkyl-$OR^4$, $-CN$, $-SR^4$, $-NR^4R^5$, or $-C(O)NR^4R^5$. In these compounds, x can be 1 and T can be O.

A further subset of the compounds are featured by that x is 1 and T is O.

Yet still another subset of the compounds are featured by that y is 1, and W is $-(CH_2)_2-O-$ or $-(CH_2)_3-O-$. These compounds include those in which x is 1 and T is O; those in which each of $R^1$ and $R^3$, independently, is $C_{6-12}$ aryl, $C_{6-12}$ aralkyl, or heteroaryl, optionally substituted with halogen, $-OR^4$, $C_{1-4}$ alkyl, $C_{1-4}$ haloalkyl, $C_{1-4}$ alkyl-$OR^4$, $-CN$, $-SR^4$, $-NR^4R^5$, $-NR^4C(O)NR^5R^6$, or $R^7$, $R^7$ being $C_{6-12}$ aryl or heteroaryl, optionally substituted with $C_{1-4}$ haloalkyl, halogen, $-OR^4$, or $-NO_2$; and those in which $R^2$ is H, $C_{1-5}$ alkyl, $C_{1-5}$ haloalkyl, $C_{6-12}$ aryl, $C_{6-12}$ aralkyl, or heteroaryl, optionally substituted with halogen, $-OR^4$, $C_{1-4}$ alkyl, $C_{1-4}$ haloalkyl, $C_{1-4}$ alkyl-$OR^4$, $-CN$, $-SR^4$, $-NR^4R^5$, or $-C(O)NR^4R^5$. They further include compounds in which each of $R^1$ and $R^3$, independently, is pyridinyl, phenyl, or thiazolyl, optionally substituted with halogen, —OR$^4$, $C_{1-4}$ alkyl, $C_{1-4}$ haloalkyl, $C_{1-4}$ alkyl-OR$^4$, —CN, —SR$^4$, —NR$^4$R$^5$, —NR$^4$C(O)NR$^5$R$^6$, or R$^7$, wherein R$^7$ is $C_{6-12}$ aryl or heteroaryl, optionally substituted with $C_{1-4}$ haloalkyl, halogen, —OR$^4$, or —NO$_2$. Examples of such compounds include:

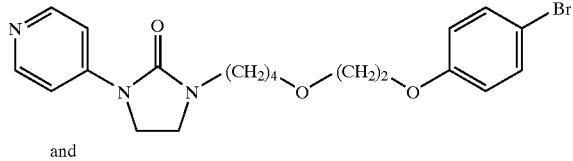

and

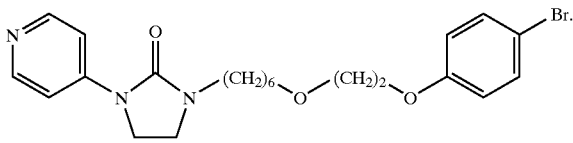

Still a further subset of the compounds are featured by that y is 0. These compounds include those in which each of R$^1$ and R$^3$, independently, is $C_{6-12}$ aryl, $C_{6-12}$ aralkyl, or heteroaryl, optionally substituted with halogen, —OR$^4$, $C_{1-4}$ alkyl, $C_{1-4}$ haloalkyl, $C_{1-4}$ alkyl-OR$^4$, —CN, —SR$^4$, —NR$^4$R$^5$, —NR$^4$C(O)NR$^5$R$^6$, or R$^7$, wherein R$^7$ is $C_{6-12}$ aryl or heteroaryl, optionally substituted with $C_{1-4}$ haloalkyl, halogen, —OR$^4$, or —NO$_2$; those in which R$^2$ is H, $C_{1-5}$ alkyl, $C_{1-5}$ haloalkyl, $C_{6-12}$ aryl, $C_{6-12}$ aralkyl, or heteroaryl, optionally substituted with halogen, —OR$^4$, $C_{1-4}$ alkyl, $C_{1-4}$ haloalkyl, $C_{1-4}$ alkyl-OR$^4$, —CN, —SR$^4$, —NR$^4$R$^5$, or —C(O)NR$^4$R$^5$; those in which x is 1, and T is O. They also include compounds in which each of R$^1$ and R$^3$, independently, is pyridinyl, phenyl, or thiazolyl, optionally substituted with halogen, —OR$^4$, $C_{1-4}$ alkyl, $C_{1-4}$ haloalkyl, $C_{1-4}$ alkyl-OR$^4$, —CN, —SR$^4$, —NR$^4$R$^5$, —NR$^4$C(O)NR$^5$R$^6$, or R$^7$, and R$^7$ is $C_{6-12}$ aryl or heteroaryl, optionally substituted with $C_{1-4}$ haloalkyl, halogen, —OR$^4$, or —NO$_2$. Examples of such compounds include:

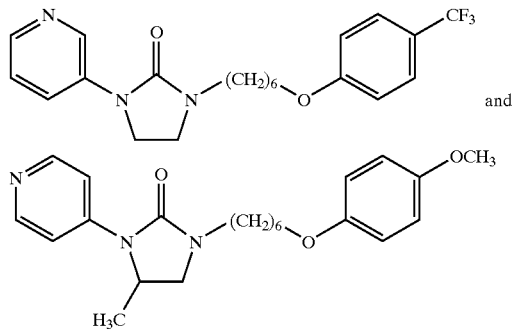

The compounds described above include their pharmaceutically acceptable salts and prodrugs, if applicable. Such a salt can be formed between a negatively charged ionic group in an imidazolidinone compound (e.g., carbonate) and a positively charged counterion (e.g., sodium, potassium, calcium, or magnesium). Likewise, a positively charged ionic group in an imidazolidinone compound (e.g., ammonium) can also form a salt with a negatively charged counterion (e.g., chloride, bromide, or iodide). Examples of such imidazolidinone salts include the sodium salt of 1-(4-pyridyl)-3-(6-[4-(trifluoromethyl)phenoxy]hexyl)-5-carboxyethyl-2-imidazolidinone and the chloride salt of 1-[7-(4-aminophenoxy)heptyl]-3-(4-pyridyl)-2-imidazolidinone. Examples of prodrugs include esters and other pharmaceutically acceptable compounds, which, upon administration to a subject, are capable of providing imidazolidinone compounds described above.

The compounds of this invention can be used as antiviral agents, particularly against a human enterovirus. Accordingly, another aspect of this invention relates to imidazolidinone compounds as agents against infections of enteroviruses; a method of treating infection by an enterovirus, i.e., administering to a subject in need thereof an effective amount of an imidazolidinone compound described above; and a method of using such an imidazolidinone compound to manufacture a medicament used in treating infection by an enterovirus. The invention also relates to a composition containing an imidazolidinone compound described above and a pharmaceutically acceptable carrier.

The details of many embodiments of the invention are set forth in the description below. Other features, objects, and advantages of the invention will be apparent from the description and the claims.

DETAILED DESCRIPTION

The imidazolidinones of this invention generally can be prepared by one of the following two methods: (1) N-(2-chloroethyl)urea in the presence of a suitable base gave rise to the imidazolidinone precursor (See Otto Meth-Cohn et al., *J. Chem. Soc., Perkin Trans.* 1, 1998, 423–436) followed by alkylation reaction; and (2) intramolecular cyclization of N-(2-hydroxyethyl) cyanoguanidine by activating its hydroxyl group (See, e.g., Taek Hyeon Kim et al., *J. Org. Chem.*, 1999, 64:2941–2943; and Taek Hyeon Kim et al., *Syn. Commun.*, 1999, 29(16):2753–2758) resulted in the formation of a 4-substituted cyanoguanidine intermediate which was then applied to alkylation reactions. Shown below are two schemes which respectively depict these two different methods. In both schemes, R$^1$, R$^2$, R$^3$, m, T, and x are as defined above; and n is 1–4.

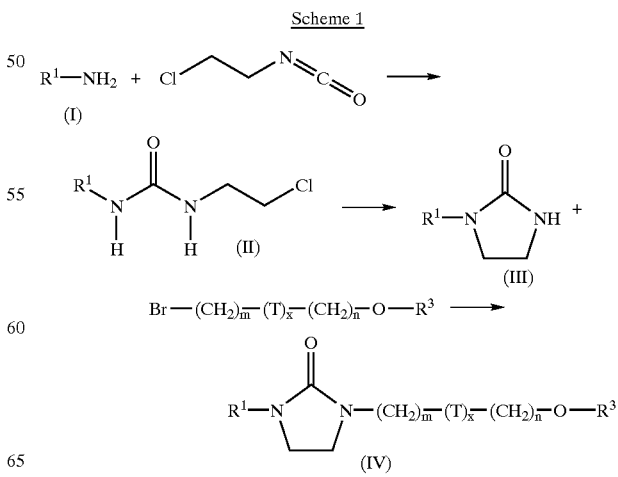

Scheme 2

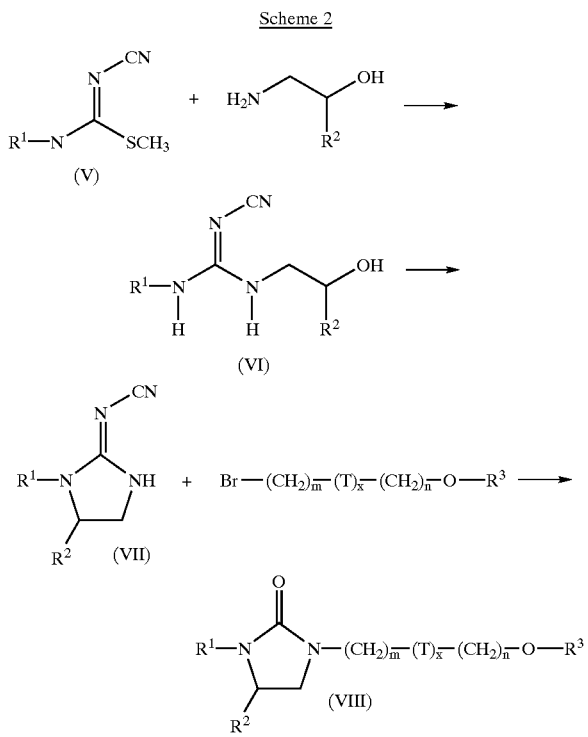

In Scheme 2, one of the common starting materials, i.e., S-methyl-N-cyano-N'-pyridylisothiourea (V), can be readily prepared by coupling 4-amino pyridine with dimethyl N-cyanodithioiminocarbonate according to well-known methods. See, e.g., Charlotte Schou et al., *Bioorganic & Medicinal Chemistry Letters*, 1997, 7(24):3095–3100.

Other imidazolidinone compounds of this invention (e.g., referring to the generic formula, those in which y is 0) can also be synthesized by either of the two methods described above, by using a suitable alkylating agent, e.g., Br—$(CH_2)_m$—$(T)_x$—$R^3$.

An imidazolidone compound thus prepared can be preliminarily screened by an in vitro inhibition assay (e.g., plaque reduction assay) for its activity against viruses, and particularly, enteroviruses. A compound that demonstrates high activity in the preliminary screening can be further evaluated by in vivo methods well known in the art (see, e.g., Daniel C. Pevear et al., *Antimicrobial Agents & Chemotherapy*, 1999, 43(9): 2109–2115).

A suitable imidazolidinone compound, its salt, or its prodrug in an effective amount is formulated with a pharmaceutically acceptable carrier to form a pharmaceutical composition before it is administered to a subject in need of an antivirus treatment. "An effective amount" refers to the amount of the compound which is required to confer therapeutic effect on the treated subject. The effective amount varies, as recognized by those skilled in the art, depending on factors such as the route of administration, the excipient usage, the distance of tumor from the skin surface, the source of the irradiation, and the optional co-usage with other therapeutic treatments including use of other antitumor compounds. Examples of pharmaceutically acceptable carriers include water, colloidal silica oxide, magnesium sterate, lipid, lipoprotein, blood protein, and cellulose.

The pharmaceutical composition may be administered via a parenteral route, e.g., topically, intraperitoneally, and intravenously. Examples of parenteral dosage forms include an active compound dissolved in phosphate buffered saline (PBS), or admixed with any other pharmaceutically acceptable carrier. Solubilizing agents, such as cyclodextrins, or other solubilizing agents well known to those familiar with the art, can also be included in the pharmaceutical composition.

Without further elaboration, it is believed that one skilled in the art, based on the description herein, can utilize the present invention to its fullest extent. The following specific examples, which described synthesis and biological testing of imidazolidinone compounds, are therefore to be construed as merely illustrative, and not limitative of the remainder of the disclosure in any way whatsoever.

EXAMPLE 1

Synthesis of 1-(4-pyridyl)-3-(6-[4-(trifluoromethyl)phenoxy]hexyl)-2-imidazolidinone (Compound 1)

A suspension of 1-(4-pyridyl)-2-imidazolidinone (0.10 g, 0.61 mmol) and sodium hydride (75% dispersion in mineral oil, 0.02 g, 0.67 mmol) in anhydrous DMF (7 mL) was cooled in an ice bath and stirred at 0° C. for 30 minutes, followed by addition of a solution of 1-bromo-6-[4-(trifluoromethyl)-phenoxy]hexane (0.20 g, 0.61 mmol) in anhydrous DMF (3 mL). After 5 minutes, the ice bath was removed and the reaction mixture was stirred at room temperature for 3 hours. The reaction was quenched with a saturated aqueous ammonium chloride solution followed by extraction with a mixture of diethyl ether and ethyl acetate (3:1, 100 mL×3). The organic layers were combined and washed with brine, dried over magnesium sulfate, and concentrated under reduced pressure. The crude mixture thus obtained was purified with gradient chromatography [100% ethyl acetate, and, subsequently, a mixture of ethyl acetate and methanol (4:1)] to yield the product (i.e., Compound 1) as a white solid (0.18 g, 73%).

$^1$H-NMR (CDCl$_3$, ppm): 8.42 (d, 2H), 7.51–7.44 (m, 4H), 6.91 (d, 2H), 3.97 (t, 2H), 3.79 (dd, 2H), 3.51 (dd, 2H), 3.31 (t, 2H), 1.82–1.75 (m, 2H), 1.64–1.37 (m, 6H).

ESMS 408.5 (M+1), 430.5 (M+23).

EXAMPLE 2

Synthesis of 1-[7-(4-chlorophenoxy)heptyl]-3-(4-pyridyl)-2-imidazolidinone (Compound 2)

To a solution of 1-(4-pyridyl)-2-imidazolidinone (0.10 g, 0.62 mmol) dissolved in 10 mL dimethylformamide cooled in an ice bath was added NaH (60% dispersion in mineral oil, 27.2 mg, 0.68 mmol). The mixture was stirred at room temperature for 30 minutes then cooled in ice bath again. 1-Bromo-7-(4-chlorophenoxy)heptane (0.19 g, 0.62 mmol) was added, and the mixture was stirred at room temperature for additional 4 hours. The reaction was quenched with methanol, and the solvent was removed under reduced pressure. 5 mL of saturated aqueous NH$_4$Cl solution and 10 mL dichloromethane were successively added to the residue. The dichloromethane layer was separated and dried over MgSO$_4$, filtered, evaporated, and purified by column chromatography (ethyl acetate:MeOH=10:1) to give the product (i.e., Compound 2) as a white solid (0.15 g, 62%).

$^1$H-NMR (CDCl$_3$, ppm): 8.40 (d, 2H), 7.46 (d, 2H), 7.18 (d, 2H), 6.77 (d, 2H), 3.87 (t, 2H), 3.76 (dd, 2H), 3.49 (dd, 2H), 3.27 (t, 2H), 1.76–1.71 (m, 2H), 1.57–1.52 (m, 2H), 1.43–1.35 (m, 6H).

ESMS 388.3 (M+1), 410.1 (M+23).

EXAMPLE 3

Synthesis of 1-4-[3-(4-methoxyphenoxy)propoxy]butyl-3-(4-pyridyl)-2-imidazolidinone (Compound 3)

To a solution of 1-(4-pyridyl)-2-imidazolidinone (0.10 g, 0.60 mmol) dissolved in 10 mL dimethylformamide cooled in an ice bath was added NaH (60% dispersion in mineral oil, 26.6 mg, 0.67 mmol). The mixture was stirred at room temperature for 30 minutes and then cooled in ice bath again. 1-[3-(4-Bromobutoxy)propoxy]-4-methoxybenzene (0.18 g, 0.60 mmol) was added, and the mixture was stirred at room temperature for additional 4 hours. The reaction was quenched with methanol, and the solvent was removed under vacuum. A saturated aqueous $NH_4Cl$ solution and 10 mL dichloromethane were successively added to the residue. The dichloromethane layer was separated and dried over $MgSO_4$, filtered, evaporated, and purified by column chromatography (ethyl acetate:methanol=10:1) to give the product (i.e., Compound 3) as a white solid (0.16 g, 69%).

$^1$H-NMR ($CDCl_3$, ppm): 8.32 (d, 2H), 7.37 (d, 2H), 6.72 (s, 4H), 3.90 (t, 2H), 3.63–3.59 (m, 5H), 3.49 (t, 2H), 3.39–3.34 (m, 4H), 3.20 (t, 2H), 1.93–1.89 (m, 2H), 1.53–1.51 (m, 4H).

ESMS 400.2 (M+1), 422.2 (M+23).

EXAMPLE 4

Synthesis of 1-[6-(1,3-benzothiazol-2-yloxy)hexyl]-3-(3-pyridyl)-2-imidazolidinone (Compound 4)

To a solution of 1-(3-pyridyl)-2-imidazolidinone (0.11 g, 0.65 mmol) dissolved in 10 mL dimethylformamide cooled in an ice bath was added NaH (60% dispersion in mineral oil, 31.2 mg, 0.78 mmol). The mixture was stirred at room temperature for 30 minutes and then cooled in ice bath again. 2-[(6-Bromohexyl)oxy]-1,3-benzothiazole (0.20 g, 0.65 mmol) was added, and the mixture was stirred at room temperature for additional 4 hours. The reaction was quenched with MeOH, and the solvent was removed under vacuum. A saturated aqueous $NH_4Cl$ solution (5 mL) and dichloromethane (10 mL) were successively added to the residue. The dichloromethane layer was separated and dried over $MgSO_4$, filtered, evaporated, and purified by column chromatography (ethyl acetate:MeOH=10:1) to give the product (i.e., Compound 4) as a white solid (0.14 g, 88%).

$^1$H-NMR ($CDCl_3$, ppm): 8.61 (bs, 1H), 8.26–8.21 (m, 2H), 7.40 (d, 1H), 7.29–7.26 (m, 2H), 7.16 (t, 1H), 7.02 (d, 1H), 3.93 (t, 2H), 3.83 (dd, 2H), 3.51 (dd, 2H), 3.28 (t, 2H), 1.76–1.71 (m, 2H), 1.58–1.39 (m, 6H).

ESMS 397.5 (M+1), 419.5 (M+23).

EXAMPLE 5

Synthesis of 1-[6-(2,6-dichloro-4-methylphenoxy)hexyl]-3-(3-pyridyl)-2-imidazolidinone (Compound 5)

To a solution of 1-(3-pyridyl)-2-imidazolidinone (0.10 g, 0.63 mmol) dissolved in 10 mL dimethylformamide cooled in an ice bath was added NaH (60% dispersion in mineral oil, 38.2 mg, 0.96 mmol). The mixture was stirred at room temperature for 30 minutes and then cooled in ice bath. 2-[(6-Bromohexyl)oxy]-1,3-dichloro-5-methylbenzene (0.22 g, 0.64 mmol) was added, and the mixture was stirred at room temperature for additional 4 hours. The reaction was quenched with MeOH, and the solvents were pumped off. 5 mL of a saturated aqueous $NH_4Cl$ solution and 10 mL of dichloromethane were successively added to the residue. The dichloromethane layer was separated and dried over $MgSO_4$, filtered, evaporated, and purified by column chromatography (ethyl acetate:MeOH=10:1) to give the product (i.e., Compound 5) as a white solid (0.36 g, 90%).

$^1$H-NMR ($CDCl_3$, ppm): 8.57 (bs, 1H), 8.22 (bs, 1H), 8.16 (d, 1H), 7.23–7.19 (m, 1H), 7.03 (s, 2H), 3.93 (t, 2H), 3.80 (dd, 2H), 3.47 (dd, 2H), 3.35–3.26 (m, 2H), 2.22 (s, 3H), 1.83–1.76 (m, 2H), 1.60–1.37 (m, 6H).

ESMS 422.5 (M+1), 444.4 (M+23).

EXAMPLE 6

Synthesis of 1-(4-chlorophenyl)-3-(5-[3-(4-methoxyphenoxy)propoxy]pentyl)-2-imidazolidinone (Compound 6)

To a solution of 1-(4-chlorophenyl)-2-imidazolidinone (0.10 g, 0.53 mmol) dissolved in 10 mL dimethylformamide cooled in an ice bath was added NaH (60% dispersion in mineral oil, 27.3 mg, 0.80 mmol). The mixture was stirred at room temperature for 30 min and then cooled in ice bath. 1-{3-[(5-Bromopentyl)oxy]propoxy}-4-methoxybenzene (0.18 g, 0.53 mmol) was added, and the mixture was stirred at room temperature for additional 4 hours. The reaction was quenched with MeOH, and the solvents were pumped off. 5 mL saturated aqueous $NH_4Cl$ solution and 10 mL dichloromethane were successively added to the residue. The dichloromethane layer was separated and dried over $MgSO_4$, filtered, evaporated, and purified by column chromatography (ethyl acetate:MeOH=10:1) to give the product (i.e., Compound 6) as a white solid (0.16 g, 68%).

$^1$H-NMR ($CDCl_3$, ppm): 7.45 (d, 2H), 7.24 (d, 2H), 6.80 (s, 4H), 3.97 (t, 2H), 3.74–3.69 (m, 5H), 3.55 (t, 2H), 3.53–3.39 (m, 4H), 3.24 (t, 2H), 2.03–1.97 (m, 2H), 1.62–1.50 (m, 4H), 1.40–1.34 (m, 2H).

ESMS 447.1 (M+1), 469.1 (M+23).

EXAMPLE 7

Synthesis of 1-[6-(4-bromophenoxy)hexyl]-3-(4-fluorophenyl)-2-imidazolidinone (Compound 7)

To a solution of 1-(4-fluorophenyl)-2-imidazolidinone (0.12 g, 0.65 mmol) dissolved in 10 mL dimethylformamide cooled in an ice bath was added NaH (60% dispersion in mineral oil, 39.0 mg, 0.98 mmol). The mixture was stirred at room temperature for 30 minutes and then cooled in ice bath. 1-Bromo-6-(4-bromophenoxy)heptane (0.22 g, 0.65 mmol) was added, and the mixture was stirred at room temperature for additional 4 hours. The reaction was quenched with methanol, and the solvents were removed under reduced pressure. 5 mL of saturated $NH_4Cl$ water solution and 10 mL of dichloromethane were added to the residue. The dichloromethane layer was dried over $MgSO_4$, filtered, evaporated, and purified by column chromatography (ethyl acetate:MeOH=10:1) to give the product (i.e., Compound 7) as a white solid (0.14 g, 48%).

$^1$H-NMR ($CDCl_3$, ppm): 7.48 (dd, 2H), 7.34 (d, 2H), 7.02 (t, 2H), 6.75 (d, 2H), 3.91 (t, 2H), 3.78 (dd, 2H), 3.46 (dd, 2H), 3.29 (t, 2H), 1.78–1.38 (m, 8H).

ESMS 435.1 (M+1), 457.1 (M+23).

EXAMPLE 8

Synthesis of 1-[7-(4-bromophenoxy)heptyl]-3-(2-chloro-4-pyridyl)-2-imidazolidinone (Compound 8)

To a solution of 1-(2-chloro-4-pyridyl)-2-imidazolidinone (0.12 g, 0.63 mmol) dissolved in 10 mL dimethylformamide at 0° C. was added NaH (60% dispersion in mineral oil, 27.7 mg, 0.69 mmol). The mixture was stirred at room temperature for 30 minutes; then cooled in ice bath. 1-Bromo-4-[(7-bromoheptyl)oxy] benzene (0.22 g, 0.63 mmol) was added, and the mixture was stirred at room temperature for additional 4 hours. The reaction was quenched with MeOH, and the solvents were pumped off. A saturated aqueous $NH_4Cl$ solution (5 mL) and dichloromethane (10 mL) were added to the residue. The dichloromethane layer was dried over $MgSO_4$, filtered, evaporated, and purified by column chromatography (ethyl acetate:MeOH=10:1) to give the product (i.e., Compound 8) as a white solid (0.19 g, 64%).

$^1$H-NMR ($CDCl_3$, ppm): 8.16 (d, 1H), 7.46–7.45 (m, 2H), 7.33 (d, 2H), 6.74 (d, 2H), 3.88 (t, 2H), 3.75 (dd, 2H), 3.51 (dd, 2H), 3.28 (t, 2H), 1.77–1.72 (m, 2H), 1.58–1.37 (m, 8H).

ESMS 467.4 (M+1).

EXAMPLE 9

Synthesis of 1-[5-(4-bromophenoxy)pentyl]-3-phenyl-2-imidazolidinone (Compound 9)

To a solution of 1-phenyl-2-imidazolidinone (0.10 g, 0.62 mmol) dissolved in 10 mL dimethylformamide cooled in an ice bath was added NaH (60% dispersion in mineral oil, 27.0 mg, 0.68 mmol). The mixture was stirred at room temperature for 30 minutes; then cooled in ice bath. 1-Bromo-4-[(5-bromopentyl)oxy] benzene (0.20 g, 0.62 mmol) was added, and the mixture was stirred at room temperature for additional 4 hours. The reaction was quenched with MeOH, and the solvents were pumped off. Saturated aqueous $NH_4Cl$ and dichloromethane (15 mL) were added to the residue. The dichloromethane layer was separated and dried over $MgSO_4$, filtered, evaporated, and purified by column chromatography (ethyl acetate:MeOH=10:1) to give the product (i.e., Compound 9) as a yellow solid (0.19 g, 77%).

$^1$H-NMR ($CDCl_3$, ppm): 7.50 (d, 2H), 7.31–7.26 (m, 4H), 6.97 (dd, 1H), 6.70 (d, 2H), 3.85 (t, 2H), 3.69 (dd, 2H), 3.37 (dd, 2H), 3.25 (t, 2H), 1.81–1.72 (m, 2H), 1.60–1.43 (m, 4H).

ESMS 403.1 (M+1), 425.0 (M+23).

EXAMPLE 10

Synthesis of 1-[6-(4-bromophenoxy)hexyl]-3-(4-methyl-1,3-thiazol-2-yl)-2-imidazolidinone (Compound 10)

To a suspension of 1-(4-methyl-1,3-thiazol-2-yl)-2-imidazolidinone (0.11 g, 0.61 mmol) dissolved in 10 mL of dimethylformamide at 0° C. was added NaH (60% dispersion in mineral oil, 36.6 mg, 0.92 mmol). The mixture was stirred at room temperature for 30 minutes and then cooled in ice bath. 1-Bromo-4-[(6-bromohexyl)oxy] benzene (0.21 g, 0.61 mmol) was added, and the mixture was stirred at room temperature for additional 4 hours. The reaction was quenched with methanol, and the solvents were removed under reduced pressure. A saturated aqueous $NH_4Cl$ solution and dichloromethane were successively added to the residue. The dichloromethane layer was separated and dried over $MgSO_4$, filtered, evaporated, and purified by column chromatography (ethyl acetate:MeOH=10:1) to give the product (i.e., Compound 10) as a yellow viscous oil (0.19 g, 74%).

$^1$H-NMR ($CDCl_3$, ppm): 7.30 (d, 2H), 6.71 (d, 2H), 6.37 (s, 1H), 4.04 (t, 2H), 3.85 (dd, 2H), 3.49 (dd, 2H), 3.27 (t, 2H), 2.28 (s, 3H), 1.75–1.70 (m, 2H), 1.58–1.35 (m, 6H).

ESMS 438.4 (M+1).

EXAMPLE 11

Synthesis of 1-(6-[(5-chloro-3-pyridyl)oxy]hexyl)-3-(4-pyridyl)-2-imidazolidinone (Compound 11)

To a solution of 1-(4-pyridyl)-2-imidazolidinone (100 mg, 0.61 mmol) and 3-[(6-bromohexyl)oxy]-5-chloropyridine (269 mg, 0.92 mmol) in DMF (5 mL) was added sodium hydride (39 mg, 1.23 mmol, 75% in mineral oil) in an ice bath. The mixture was stirred at room temperature overnight. After removing the solvent under reduced pressure, the crude residue was purified by column chromatography eluted with 15% methanol in ethyl acetate to afford the product (i.e., Compound 11) as a light yellow solid (0.17 g, 75%).

$^1$H-NMR ($CDCl_3$, ppm): 8.40 (d, 2H), 8.15–8.12 (m, 2H), 7.54 (d, 2H), 7.15 (t, 1H), 3.96 (t, 2H), 3.82 (dd, 2H), 3.53 (dd, 2H), 3.30 (t, 2H), 1.83–1.73 (m, 2H).

ESMS 375.1 (M+1).

EXAMPLE 12

Synthesis of [5-methyl-1-(4-pyridyl)tetrahydro-1H-2-imidazolyliden] aminomethane-nitrile (Compound 12)

To a mixture of N-(2-methyl-2-hydroxyethyl)-N'-cyano-N''-4-pyridylguanidine (0.5 g, 2.2 mmol) and triphenylphosphine (1.2 g, 4.5 mmol) in THF (20 mL) at 0° C. under nitrogen was added diisopropyl azodicarboxylate (0.92 g, 4.5 mmol) dissolved in THF (10 mL) dropwise over 15 minutes. The resulting mixture was stirred at 0° C. for another 2 hours and then warmed to room temperature for 60 hours. After the reaction was complete, the mixture was concentrated and purified by chromatography on silica gel using ethyl acetate as eluant to remove triphenylphosphine and triphenylphosphine oxide followed by elution with a mixture of dichloromethane and methanol (7:1) to afford the product (i.e., Compound 12) as a white solid (0.23 g, 50%).

$^1$H-NMR ($CDCl_3$, ppm): 8.77 (bs, 1H), 8.47 (d, 2H), 7.56 (d, 2H), 4.79–4.74 (m, 1H), 3.78 (t, 1H), 3.24–3.19 (m, 1H), 1.22 (d, 3H).

ESMS 202.1 (M+1), 224.1 (M+23).

EXAMPLE 13

Synthesis of 1-[6-(4-fluorophenoxy)hexyl]-4-methyl-3-(4-pyridyl)-2-imidazolidinone (Compound 13)

To a solution of [5-methyl-1-(4-pyridyl)tetrahydro-1H-2-imidazolyliden]amino methanenitrile (60 mg, 0.30 mmol) in DMF (5 mL) at 0° C. was added sodium hydride (19 mg, 0.60 mmol, 75% in mineral oil) in one portion. The mixture was stirred at room temperature for 20 min followed by addition of 1-[(6-bromohexyl)oxy]-4-fluorobenzene (123 mg, 0.45 mmol) dissolved in DMF (3 ml) drop by drop. The resulting mixture was heated to 80° C. and stirred overnight (16 hours). The solvent was removed under reduced pressure and the crude residue was purified by column chromatography eluting with 15% methanol in ethyl acetate to afford the product (i.e., Compound 13) as a white solid (44 mg, 37%).

$^1$H-NMR ($CDCl_3$, ppm): 8.39 (d, 2H), 7.45 (d, 2H), 6.94–6.88 (m, 2H), 6.79–6.75 (m, 2H), 4.35–4.25 (m, 1H), 3.87 (t, 2H), 3.61 (t, 1H), 3.34 (dt, 1H), 3.19 (dt, 1H), 3.05 (dd, 1H), 1.78–1.69 (m, 2H), 1.61–1.31 (m, 9H).

ESMS 372.5 (M+1), 394.5 (M+23).

EXAMPLE 14

Synthesis of [5-phenyl-1-(4-pyridyl)tetrahydro-1H-2-imidazolyliden]aminomethane-nitrile (Compound 14)

To a solution of N-(2-phenyl-2-hydroxyethyl)-N'-cyano-N''-4-pyridylguanidine (1.0 g, 3.56 mmol) and triphenylphosphine (1.86 g, 7.12 mmol) in THF (30 mL) at 0° C. was added diisopropyl azodicarboxylate (3.8 mL, 7.12 mmol) dissolved in 15 mL (THF) by syringe pump over 30 min. The resulting mixture was kept stirring and warmed to room temperature for 70 h. The product was precipitated from ether to form the white solid. The solid thus obtained was washed sequentially with ether, methanol and acetone to give the product (i.e., Compound 14) as a white solid (0.67 g, 72%).

$^1$H-NMR ($CDCl_3$, ppm): 9.01 (bs, 1H), 8.35 (d, 2H), 7.45 (d, 2H), 7.35–7.26 (m, 5H), 5.79 (dd, 1H), 4.10 (t, 1H), 3.33–3.28 (m, 1H).

ESMS 264.2 (M+1), 286.1 (M+23).

EXAMPLE 15

Synthesis of 1-[6-(4-bromophenoxy)hexyl]-4-phenyl-3-(4-pyridyl)-2-imidazolidinone (Compound 15)

To a solution of [5-phenyl-1-(4-pyridyl)tetrahydro-1H-2-imidazolyliden] aminomethane-nitrile (0.1 g, 0.38 mmol) in 6 mL of DMF at 0° C. was added sodium hydride (75% dispersion in mineral oil, 24 mg) in one portion. The mixture was stirred at room temperature for 20 min and then 1-[(6-bromohexyl)oxy]-4-bromobenzene (192 mg, 0.57 mmol) dissolved in DMF (4 mL) was added dropwise. The resulting mixture was stirred and heated at 80° C. for 16 hours. The reaction was quenched with water and aqueous solution was extracted with ether (3×20 mL). The organic layers were combined, washed with NaCl(sat.), dried over MgSO$_4$, and concentrated under reduced pressure to give the crude residue, which was subjected to purification by chromatography elution with ethyl acetate and methanol (20:1) to afford the product (i.e., Compound 15) as a white solid (90 mg, 45%).

$^1$H-NMR (CDCl$_3$, ppm): 8.28 (d, 2H), 7.40 (d, 2H), 7.36–7.21 (m, 7H), 6.72 (d, 2H), 5.13 (dd, 1H), 3.93–3.84 (m, 3H), 3.41–3.20 (m, 3H), 1.76–1.67 (m, 2H), 1.58–1.29 (m, 6H).

ESMS 494.1 (M+1).

EXAMPLES 16–76

Synthesis of Additional Imidazolidinone Compounds

Each of the imidazolidinone compounds named in the following table was prepared in accordance with the methods described above. $^1$H nuclear magnetic resonance (NMR) and mass spectroscopy data, and the method of synthesizing each compound are also listed below. The columns "Mass (Cald.)," "M+1," and "Mass+23" refer to the calculated mass, the measured mass, and the mass associated with Na$^+$, of the named compounds, respectively.

| Example (Cpd ID) | Name | NMR (CDCl$_3$, ppm) | Mass (Cald.) | M + 1 | Mass + 23 | Method |
|---|---|---|---|---|---|---|
| 16 | 1-(4-pyridyl)-3-[6-(8-quinolyloxy)hexyl]-2-imidazolidinone | 8.91 (dd, 1H), 8.41 (d, 2H), 8.09 (dd, 1H), 7.45-7.32 (m, 5H), 7.02 (dd, 1H), 4.21 (t, 2H), 3.75 (dd, 2H), 3.49 (dd, 2H), 3.30 (t, 2H), 2.07-1.91 (m, 2H), 1.65-1.21 (m, 6H) | 390.2 | 391.2 | 413.3 (M + 23) | 1 |
| 17 | 1-[6-(4-bromophenoxy) hexyl]-3-(4-pyridyl)-2-imidazolidinone | 8.42 (d, 2H), 7.45 (d, 2H), 7.32 (d, 2H), 6.73 (d, 2H), 3.89 (t, 2H), 3.78 (dd, 2H), 3.51 (dd, 2H), 3.30 (t, 2H), 1.78-1.71 (m, 2H), 1.64-1.38 (m, 6H) | 417.1 | 418.4 | 440.4 (M + 23) | 1 |
| 18 | 1-[6-(4-fluorophenoxy) hexyl]-3-(4-pyridyl)-2-imidazolidinone | 8.42 (d, 2H), 7.46 (d, 2H), 6.96-6.90 (m, 2H), 6.81-6.77 (m, 2H), 3.89 (t, 2H), 3.79 (dd, 2H), 3.51 (dd, 2H), 3.30 (1, 2H), 1.78-1.73 (m, 2H), 1.61-1.23 (m, 6H) | 357.2 | 358.4 | 380.5 (M + 23) | 1 |
| 19 | 1-[6-(4-methylphenoxy) hexyl]-3-(4-pyridyl)-2-imidazolidinone | 8.42 (d, 2H), 7.45 (d, 2H), 7.04 (d, 2H), 6.76 (d, 2H), 3.91 (t, 2H), 3.78 (dd, 2H), 3.51 (dd, 2H), 3.30 (t, 2H), 2.26 (s, 3H), 1.78-1.30 (m, 8H) | 353.2 | 354.5 | 376.5 (M + 23) | 1 |
| 20 | 1-6-[4-(tert-butyl)phenoxy]hexyl-3-(4-pyridyl)-2-imidazolidinone | 8.42 (d, 2H), 7.46 (d, 2H), 7.26 (d, 2H), 6.80 (d, 2H), 3.92 (t, 2H), 3.78 (dd, 2H), 3.51 (dd, 2H), 3.30 (t, 2H), 1.81-1.39 (m, 17H) | 395.3 | 396.5 | 418.5 (M + 23) | 1 |
| 21 | 1-[6-(4-chlorophenoxy)hexyl]-4-methyl-3-(4-pyridyl)-2-imidazolidinone | 8.39 (d, 2H), 7.47 (d, 2H), 7.15 (d, 2H), 6.75 (d, 2H), 4.34-4.24 (m, 1H), 3.87 (t, 2H), 3.60 (t, 1H), 3.34 (dt, 1H), 3.19 (dt, 1H), 3.04 (dd, 1H), 1.78-1.69 (m, 2H), 1.60-1.30 (m, 9H) | 387.2 | 388.1 | 410.1 (M + 23) | 2 |
| 22 | 1-[6-(4-methoxyphenoxy) hexyl]-3-(4-pyridyl)-2-imidazolidinone | 8.41 (d, 2H), 7.48 (d, 2H), 6.79 (s, 4H), 3.87 (t, 2H), 3.78 (dd, 2H), 3.73 (s, 3H), 3.51 (dd, 2H), 3.30 (t, 2H), 1.79-1.70 (m, 2H), 1.63-1.23 (m, 6H) | 369.2 | 370.2 | 392.2 (M + 23) | 1 |
| 23 | 4-(6-[2-oxo-3-(4-pyridyl)-1-imidazolidinyl] hexyloxy)benzonitrile | 8.42 (d, 2H), 7.54 (d, 2H), 7.50 (d, 2H), 6.89 (d, 2H), 3.97 (t, 2H), 3.81 (dd, 2H), 3.53 (dd, 2H), 3.31 (t, 2H), 1.84-1.75 (m, 2H), 1.64-1.36 (m, 6H) | 364.2 | 365.1 | 387.1 (M + 23) | 1 |
| 24 | 1-[6-(4-chlorophenoxy) hexyl]-3-(4-pyridyl)-2-imidazolidinone | 8.42 (d, 2H), 7.51 (d, 2H), 7.18 (d, 2H), 6.78 (d, 2H), 3.90 (t, 2H), 3.80 (dd, 2H), 3.53 (dd, 2H), 3.30 (t, 2H), 1.81-1.71 (m, 2H), 1.63-1.35 (m, 6H) | 373.2 | 374.5 |  | 1 |
| 25 | 1-[6-(2,6-dichloro-4-methylphenoxy)hexyl]-3-(4-pyridyl)-2-imidazolidinone | 8.40 (d, 2H), 7.48 (d, 2H), 7.04 (s, 2H), 3.94 (t, 2H), 3.78 (dd, 2H), 3.52 (dd, 2H), 3.30 (t, 2H), 2.23 (s, 3H), 1.86-1.76 (m, 2H), 1.64-1.22 (m, 6H) | 421.1 | 422.5 | 444.5 (M + 23) | 1 |
| 26 | 1-(6-[3-(dimethylamino) phenoxy]hexyl)-3-(4-pyridyl)-2-imidazolidinone | 8.41 (d, 2H), 7.47 (d, 2H), 7.09 (t, 1H), 6.34-6.23 (m, 3H), 3.92 (t, 2H), 3.77 (dd, 2H), 3.50 (dd, 2H), 3.27 (t, 2H), 2.90 (s, 6H), 1.78-1.61 (m, 2H), 1.61-1.38 (m, 6H) | 382.2 | 383.5 |  | 1 |
| 27 | 1-[6-(2,6-dichlorophenoxy)hexyl]-3-(4-pyridyl)-2-imidazolidinone | 8.41 (bs. 2H), 7.50 (d, 2H), 7.25 (d, 2H), 6.95 (t, 1H), 3.99 (t, 2H), 3.80 (dd, 2H), 3.54 (dd, 2H), 3.32 (t, 2H), 1.86-1.81 (m, 2H), 1.64-1.43 (m, 6H) | 407.1 | 408.1 | 430.1 (M + 23) | 1 |
| 28 | 1-[5-(4-chlorophenoxy)pentyl]-3- | 8.41 (d, 2H), 7.46 (d, 2H), 7.18 (d, 2H), 6.78 (d, 2H), 3.90 (t, 2H), 3.77 | 359.1 | 360.4 | 382.4 (M + 23) | 1 |

-continued

| Example (Cpd ID) | Name | NMR (CDCl₃, ppm) | Mass (Cald.) | M + 1 | Mass + 23 | Method |
|---|---|---|---|---|---|---|
| | (4-pyridyl)-2-imidazolidinone | (dd, 2H), 3.51 (dd, 2H), 3.31 (t, 2H), 1.84-1.75 (m, 2H), 1.64-1.53 (m, 2H), 1.52-1.46 (m, 2H) | | | | |
| 29 | 1-[6-(1,3-benzothiazol-2-yloxy)hexyl]-3-(4-pyridyl)-2-imidazolidinone | 8.38 (d, 2H), 7.47 (d, 2H), 7.38 (d, 1H), 7.27 (t, 1H), 7.11 (t, 1H), 6.99 (d, 1H), 3.90 (t, 2H), 3.78 (dd, 2H), 3.48 (dd, 2H), 3.26 (t, 2H), 1.73-1.69 (m, 2H), 1.55-1.51 (m, 2H), 1.38-1.29 (m, 4H) | 396.2 | 397.2 | 419.2 (M + 23) | 1 |
| 30 | 4-(6-[2-(cyanoimino)-3-(4-pyridyl)-1-imidazolidinyl]hexyloxy) benzonitrile | 8.49 (bs, 2H), 7.61 (d, 2H), 7.54 (d, 2H), 6.90 (d, 2H), 4.05-3.96 (m, 4H), 3.83 (t, 2H), 3.75 (dd, 2H), 1.86-1.73 (m, 4H), 1.56-1.47 (m, 4H) | 388.2 | 389.3 | 411.2 (M + 23) | 1 |
| 31 | 4-methyl-3-(4-pyridyl)-1-(6-[4-(trifluoromethyl) phenoxy]hexyl)-2-imidazolidinone | 8.41 (d, 2H), 7.51-7.47 (m, 4H), 6.90 (d, 2H), 4.37-4.27 (m, 1H), 3.96 (t, 2H), 3.63 (t, 1H), 3.36 (dt, 1H), 3.23 (dt, 1H), 3.06 (dd, 1H), 1.83-1.74 (m, 2H), 1.63-1.33 (m, 9H) | 421.2 | 422.1 | 444.1 (M + 23) | 2 |
| 32 | 1-5-[3-(4-methoxyphenoxy)propoxy] pentyl-3-(4-pyridyl)-2-imidazolidinone | 8.39 (d, 2H), 7.78 (d, 2H), 6.80 (s, 4H), 3.97 (t, 2H), 3.90-3.82 (m, 2H), 3.74 (s, 3H), 3.59-3.53 (m, 4H), 3.42 (t, 2H), 3.31 (t, 2H), 2.02-1.94 (m, 2H), 1.65-1.53 (m, 4H), 1.43-1.33 (m, 2H) | 413.2 | 414.2 | 436.1 (M + 23) | 1 |
| 33 | 1-[6-(4-bromophenoxy) hexyl]-3-(3-pyridyl)-2-imidazolidinone | 8.55 (s, 1H), 8.18 (d, 1H), 8.02 (d, 1H), 7.23 (d, 2H), 7.14 (dd, 1H), 6.65 (d, 2H), 3.80 (t, 2H), 3.69 (dd, 2H), 3.41 (dd, 2H), 3.20 (t, 2H), 1.72-1.63 (m, 2H), 1.55-1.27 (m, 6H) | 417.1 | 418.4 | 440.4 (M + 23) | 1 |
| 34 | 1-4-[2-(4-bromophenoxy) ethoxy]butyl-3-(4-pyridyl)-2-imidazolidinone | 8.39 (bs, 2H), 7.46 (d, 2H), 7.31 (d, 2H), 6.76 (d, 2H), 4.04 (t, 2H), 3.77-3.72 (m, 4H), 3.55-3.44 (m, 4H), 3.29 (t, 2H), 1.62-1.59 (m, 2H) | 433.1 | 434.4 | 456.4 (M + 23) | 1 |
| 35 | 1-6-[4-(tert-butyl)phenoxy]hexyl-3-(3-pyridyl)-2-imidazolidinone | 8.60 (bs, 1H), 8.24-8.21 (m, 2H), 7.29-7.25 (m, 3H), 6.81 (d, 2H), 3.93 (t, 2H), 3.82 (dd, 2H), 3.51 (dd, 2H), 3.30 (t, 2H), 1.80-1.73 (m, 2H), 1.62-1.37 (m, 6H), 1.28 (s, 9H) | 395.3 | 396.5 | 418.5 (M + 23) | 1 |
| 36 | 1-[6-(4-bromophenoxy) hexyl]-3-(4-chlorophenyl)-2-imidazolidinone | 7.47 (d, 2H), 7.32 (d, 2H), 7.24 (d, 2H), 6.73 (d, 2H), 3.88 (t, 2H), 3.71 (dd, 2H), 3.39 (dd, 2H), 3.26 (t, 2H), 1.78-1.73 (m, 2H), 1.59-1.38 (m, 6H) | 450.1 | 451.4 | 473.2 (M + 23) | 1 |
| 37 | 1-[6-(4-methylphenoxy) hexyl]-3-(3-pyridyl)-2-imidazolidinone | 8.57 (bs, 1H), 8.19 (bs, 1H), 7.15 (m, 1H), 7.05 (d, 1H), 6.97 (d, 2H), 6.70 (d, 2H), 3.84 (t, 2H), 3.67 (dd, 2H), 3.39 (dd, 2H), 3.22 (t, 2H), 2.19 (s, 3H), 1.72-1.65 (m, 2H), 1.54-1.30 (m, 6H) | 353.2 | 354.5 | 376.5 (M + 23) | 1 |
| 38 | 1-[6-(4-chlorophenoxy)hexyl]-3-(3-pyridyl)-2-imidazolidinone | 8.57 (d, 1H), 8.26 (d, 2H), 7.30-7.26 (m, 1H), 7.18 (d, 2H), 6.78 (d, 2H), 3.92-3.80 (m, 4H), 3.52 (dd, 2H), 3.30 (t, 2H), 1.78-1.71 (m, 2H), 1.61-1.36 (m, 6H) | 373.2 | 374.5 | 396.4 (M + 23) | 1 |
| 39 | 1-[7-(4-chlorophenoxy) heptyl]-3-(3-pyridyl)-2-imidazolidinone | 8.56 (bs, 1H), 8.16 (bs, 1H), 8.02 (d, 1H), 7.15-7.08 (m, 3H), 6.70 (d, 2H), 3.79 (t, 2H), 3.69 (dd, 2H), 3.39 (dd, 2H), 3.18 (t, 2H), 1.68-1.64 (m, 2H), 1.49-1.30 (m, 8H) | 387.2 | 388.5 | 410.5 (M + 23) | 1 |
| 40 | 1-4-[2-(4-bromophenoxy) ethoxy]butyl-3-(4-chlorophenyl)-2-imidazolidinone | 7.44 (d, 2H), 7.30 (d, 2H), 7.22 (d, 2H), 6.76 (d, 2H), 4.03 (t, 2H), 3.74-3.65 (m, 4H), 3.52 (t, 2H), 3.39 (dd, 2H), 3.26 (t, 2H), 1.62-1.58 (m, 4H) | 466.1 | 467.4 | 489.4 (M + 23) | 1 |
| 41 | 1-[5-(4-chlorophenoxy) pentyl]-3-(3-pyridyl)-2-imidazolidinone | 8.56 (bs, 1H), 8.20 (bs, 1H), 8.09 (d, 1H), 7.20-7.11 (m, 3H), 6.73 (d, 2H), 3.85 (t, 2H), 3.74 (dd, 2H), 3.45 (dd, 2H), 3.25 (t, 2H), 1.80-1.71 (m, 2H), 1.60-1.42 (m, 4H) | 359.1 | 360.4 | 382.4 (M + 23) | 1 |
| 42 | 1-(3-pyridyl)-3-(6-[4-(trifluoromethyl)phenoxy] hexyl)-2-imidazolidinone | 8.56 (bs, 1H), 8.13 (bs, 1H), 7.95 (d, 1H), 7.37 (d, 2H), 7.11-7.07 (m, 1H), 6.79 (d, 2H), 3.83 (t, 2H), 3.66 (dd, 2H), 3.36 (dd, 2H), 3.19 (t, 2H), 1.69-1.62 (m, 2H), 1.51-1.25 (m, 6H) | 407.2 | 408.5 | 430.4 (M + 23) | 1 |
| 43 | 1-[6-(4-fluorophenoxy) hexyl]-3-(3-pyridyl)-2-imidazolidinone | 8.54 (bs, 1H), 8.11 (d, 1H), 7.95 (d, 1H), 7.08 (dd, 1H), 6.82 (d, 2H), 6.68-6.63 (m, 2H), 3.74 (t, 2H), 3.62 | 357.2 | 358.5 | 380.5 (M + 23) | 1 |

-continued

| Example (Cpd ID) | Name | NMR (CDCl$_3$, ppm) | Mass (Cald.) | M + 1 | Mass + 23 | Method |
|---|---|---|---|---|---|---|
| 44 | 1-[6-(2,6-dichlorophenoxy)hexyl]-3-(3-pyridyl)-2-imidazolidinone | (dd, 2H), 3.31 (dd, 2H), 3.14 (t, 2H), 1.67-1.57 (m, 2H), 1.47-1.22 (m, 6H) 8.54 (s, 1H), 8.26 (d, 1H), 8.13 (d, 1H), 7.16-7.11 (m, 3H), 6.84 (m, 1H), 3.90 (t, 2H), 3.70 (dd, 2H), 3.43-3.34 (m, 2H), 3.20 (t, 2H), 1.77-1.70 (m, 2H), 1.53-1.33 (m, 6H) | 407.1 | 408.4 | | 1 |
| 45 | 1-[6-(4-methoxyphenoxy)hexyl]-4-methyl-3-(4-pyridyl)-2-imidazolidinone | 8.41 (d, 2H), 7.58 (d, 2H), 6.79 (s, 4H), 4.39-4.29 (m, 1H), 3.88 (t, 2H), 3.73 (s, 3H), 3.65 (t, 1H), 3.37 (dt, 1H), 3.22 (dt, 1H), 3.08 (dd, 1H), 1.79-1.70 (m, 2H), 1.63-1.35 (m, 9H) | 383.2 | 384.2 | 406.1 (M + 23) | 2 |
| 46 | 1-[6-(2-chloro-4-methoxyphenoxy)hexyl]-3-(4-pyridyl)-2-imidazolidinone | 8.33 (d, 2H), 7.37 (d, 2H), 6.83 (d, 1H), 6.75 (d, 1H), 6.63 (dd, 1H), 3.86 (t, 2H), 3.69-3.63 (m, 5H), 3.41 (dd, 2H), 3.21 (t, 2H), 1.76-1.67 (m, 2H), 1.56-1.29 (m, 6H) | 403.2 | 404.1 | 426.1 | 1 |
| 47 | 1-(5-[2-(4-bromophenoxy)ethoxy]pentyl)-3-(4-pyridyl)-2-imidazolidinone | 8.37 (d, 2H), 7.42 (d, 2H), 7.29 (d, 2H), 6.73 (d, 2H), 4.01 (t, 2H), 3.73-3.68 (m, 4H), 3.50-3.42 (m, 4H), 3.24 (t, 2H), 1.65-1.49 (m, 4H), 1.41-1.31 (m, 2H) | 447.1 | 448.1 | | 1 |
| 48 | 1-[6-(2-chloro-4-methoxyphenoxy)hexyl]-3-(4-chlorophenyl)-2-imidazolidinone | 7.49 (d, 2H), 7.23 (d, 2H), 6.93-6.91 (m, 1H), 6.85-6.81 (m, 1H), 6.72-6.69 (m, 1H), 3.94 (t, 2H), 3.72-3.67 (m, 5H), 3.45-3.24 (m, 4H), 1.82-1.77 (m, 2H), 1.60-1.40 (m, 6H) | 436.1 | 437.1 | 459.1 (M + 23) | 1 |
| 49 | 1-[6-(1,3-benzodioxol-5-yloxy)hexyl]-3-(4-pyridyl)-2-imidazolidinone | 8.40 (d, 2H), 7.45 (d, 2H), 6.65 (d, 1H), 6.44 (s, 1H), 6.27 (d, 1H), 5.86 (s, 2H), 3.86-3.74 (m, 4H), 3.49 (dd, 2H), 3.28 (t, 2H), 1.74-1.68 (m, 2H), 1.59-1.33 (m, 6H) | 383.2 | 384.5 | 406.5 (M + 23) | 1 |
| 50 | 1-[7-(4-bromophenoxy)heptyl]-3-(4-pyridyl)-2-imidazolidinone | 8.41 (d, 2H), 7.46 (d, 2H), 7.32 (d, 2H), 6.73 (d, 2H), 3.88 (t, 2H), 3.77 (dd, 2H), 3.50 (dd, 2H), 3.28 (t, 2H), 1.76-1.71 (m, 2H), 1.69-1.34 (m, 8H) | 431.1 | 432.5 | 454.4 (M + 23) | 1 |
| 51 | 1-(4-pyridyl)-3-[6-(3,4,5-trimethoxyphenoxy)hexyl]-2-imidazolidinone | 8.37 (d, 2H), 7.43 (d, 2H), 6.08 (s, 2H), 3.86 (t, 2H), 3.79-3.71 (m, 11H), 3.47 (dd, 2H), 3.26 (t, 2H), 1.75-1.70 (m, 2H), 1.58-1.35 (m, 6H) | 429.2 | 430.5 | 452.5 (M + 23) | 1 |
| 52 | 1-[5-(4-bromophenoxy)pentyl]-3-(4-pyridyl)-2-imidazolidinone | 8.41 (d, 2H), 7.72 (d, 2H), 7.33 (d, 2H), 6.73 (d, 2H), 3.93-3.87 (m, 4H), 3.63-3.58 (m, 2H), 3.36 (t, 2H), 1.84-1.79 (m, 2H), 1.68-1.60 (m, 2H), 1.53-1.47 (m, 2H) | 403.1 | 404.4 | 426.4 (M + 23) | 1 |
| 53 | 1-[6-(1-naphthyloxy)hexyl]-3-(4-pyridyl)-2-imidazolidinone | 8.39 (d, 2H), 8.23 (d, 1H), 7.77-7.73 (m, 1H), 7.45-7.28 (m, 6H), 6.75 (d, 1H), 4.10 (t, 2H), 3.67 (dd, 2H), 3.43 (dd, 2H), 3.29 (t, 2H), 1.95-1.86 (m, 2H), 1.65-1.54 (m, 4H), 1.48-1.40 (m, 2H) | 389.2 | 390.5 | | 1 |
| 54 | 1-(6-[4-(methylsulfanyl)phenoxy]hexyl)-3-(4-pyridyl)-2-imidazolidinone | 8.40 (d, 2H), 7.50 (d, 2H), 7.21 (d, 2H), 6.80 (d, 2H), 3.90 (t, 2H), 3.79 (dd, 2H), 3.51 (dd, 2H), 3.30 (t, 2H), 2.41(s, 3H), 1.80-1.71 (m, 2H), 1.63-1.34 (m, 6H) | 385.2 | 386.5 | | 1 |
| 55 | 1-(4-pyridyl)-3-[6-(tetrahydro-2H-2-pyranyloxy)hexyl]-2-imidazolidinone | 8.29 (d, 2H), 7.35 (d, 2H), 4.44 (t, 1H), 3.77-3.57 (m, 4H), 3.42-3.22 (m, 4H), 3.17 (t, 2H), 1.75-1.24 (m, 14H) | 347.2 | 348.5 | 370.5 (M + 23) | 1 |
| 56 | 1-(2-chloro-4-pyridyl)-3-[6-(4-iodophenoxy)hexyl]-2-imidazolidinone | 8.19 (d, 1H), 7.54-7.45 (m, 4H), 6.65 (d, 2H), 3.91 (t, 2H), 3.78 (dd, 2H), 3.54 (dd, 2H), 3.32 (t, 2H), 1.80-1.75 (m, 2H), 1.62-1.40 (m, 6H) | 499.1 | 500.4 | 522.3 (M + 23) | 1 |
| 57 | 1-(2-chloro-4-pyridyl)-3-6-[4-(trifluoromethyl)phenoxy]hexyl-2-imidazolidinone | 8.15 (d, 1H), 7.50-7.41 (m, 4H), 6.90 (d, 2H), 3.95 (t, 2H), 3.74 (dd, 2H), 3.50 (dd, 2H), 3.28 (t, 2H), 1.80-1.60 (m, 2H), 1.57-1.37 (m, 6H) | 441.1 | 442.5 | 464.5 (M + 23) | 1 |
| 58 | 1-(2-chloro-4-pyridyl)-3-6-[4-(methylsulfanyl)phenoxy]hexyl-2-imidazolidinone | 8.18 (d, 1H), 7.49-7.47 (m, 2H), 7.23 (d, 2H), 6.81 (d, 2H), 3.92 (t, 2H), 3.77 (dd, 2H), 3.53 (dd, 2H), 3.30 (t, 2H), 2.42 (s, 3H), 1.81-1.72 (m, 2H), 1.64-1.38 (m, 6H) | 419.1 | 420.4 | 442.5 (M + 23) | 1 |
| 59 | 1-[5-(4-bromophenoxy)pentyl]-3-(2-chloro-4-pyridyl)-2-imidazolidinone | 8.19 (d, 1H), 7.50-7.46 (m, 2H), 7.33 (d, 2H), 6.73 (d, 2H), 3.91 (t, 2H), 3.78 (dd, 2H), 3.53 (dd, 2H), 3.32 (t, | 437.1 | 438.0 | | 1 |

-continued

| Example (Cpd ID) | Name | NMR (CDCl₃, ppm) | Mass (Cald.) | M + 1 | Mass + 23 | Method |
|---|---|---|---|---|---|---|
| | | 2H), 1.83-1.76 (m, 2H), 1.66-1.49 (m, 4H) | | | | |
| 60 | 1-[6-(4-bromophenoxy) hexyl]-3-(2-chloro-4-pyridyl)-2-imidazolidinone | 8.14 (d, 1H), 7.44-7.41 (m, 2H), 7.30(d, 2H), 6.71 (d, 2H), 3.87 (t, 2H), 3.73 (dd, 2H), 3.49 (dd, 2H), 3.27 (t, 2H), 1.76-1.71 (m, 2H), 1.58-1.36 (m, 6H) | 451.1 | 452.0 | | 1 |
| 61 | 1-[6-(4-iodophenoxy) hexyl]-3-(4-pyridyl)-2-imidazolidinone | 8.41 (d, 2H), 7.51-7.45 (m, 4H), 6.62 (d, 2H), 3.88 (t, 2H), 3.77 (dd, 2H), 3.50 (dd, 2H), 3.29 (t, 2H), 1.77-1.72 (m, 2H), 1.60-1.37 (m, 6H) | 465.1 | 466.4 | 488.4 (M + 23) | 1 |
| 62 | 3,5-dimethyl-4-(6-[2-oxo-3-(4-pyridyl)-1-imidazolidinyl]hexyloxy) benzonitrile | 8.37 (d, 2H), 7.44 (d, 2H), 7.24 (s, 2H), 3.79-3.73 (m, 4H), 3.50 (dd, 2H), 3.28 (t, 2H), 2.22 (s, 6H), 1.80-1.73 (m, 2H), 1.61-1.36 (m, 6H) | 392.2 | 393.5 | 415.5 (M + 23) | 1 |
| 63 | 1-[7-(4-bromophenoxy) heptyl]-3-(4-chlorophenyl)-2-imidazolidinone | 7.47 (d, 2H), 7.32 (d, 2H), 7.24 (d, 2H), 6.73 (d, 2H), 3.87 (t, 2H), 3.71 (dd, 2H), 3.43 (dd, 2H), 3.25 (t, 2H), 1.76-1.71 (m, 2H), 1.56-1.35 (m, 6H) | 464.1 | 465.4 | 487.4 (M + 23) | 1 |
| 64 | 1-(6-hydroxyhexyl)-3-(4-pyridyl)-2-imidazolidinone | 8.36 (bs, 2H), 7.43 (d, 2H), 3.75 (dd, 2H), 3.58 (t, 2H), 3.48 (dd, 2H), 3.25 (t, 2H), 2.78 (bs, 1H), 1.57-1.48 (m, 2H), 1.42-1.29 (m, 6H) | 263.2 | 264.4 | 286.4 (M + 23) | 1 |
| 65 | 1-(6-[(2-bromo-3-pyridyl) oxy]hexyl)-3-(4-pyridyl)-2-imidazolidinone | 8.36 (d, 2H), 7.88 (dd, 1H), 7.43 (d, 2H), 7.12 (dd, 1H), 7.05 (dd, 1H), 3.97 (t, 2H), 3.75 (dd, 2H), 3.49 (dd, 2H), 3.27 (t, 2H). 1.85-1.76 (m, 2H), 1.61-1.35 (m, 6H) | 418.1 | 419.4 | 441.4 (M + 23) | 1 |
| 66 | 1-[6-(4-chlorophenoxy) hexyl]-3-phenyl-2-imidazolidinone | 7.53 (d, 2H), 7.28 (dd, 2H), 7.18 (dd, 2H), 6.99 (dd, 1H), 6.78 (d, 2H), 3.87 (t, 2H), 3.72 (dd, 2H), 3.39 (dd, 2H), 3.26 (t, 2H), 1.80-1.70 (m, 2H), 1.61-1.35 (m, 6H) | 372.9 | 373.1 | 395.1 (M + 23) | 1 |
| 67 | 1-[6-(4-bromophenoxy) hexyl]-3-phenyl-2-imidazolidinone | 7.53 (d, 2H), 7.33-7.26 (m, 4H), 7.01 (dd, 1H), 6.72 (d, 2H), 3.85 (t, 2H), 3.69 (dd, 2H), 3.37 (dd, 2H), 3.25 (t, 2H), 1.76-1.72 (m, 2H), 1.57-1.37 (m, 6H) | 417.3 | 418.1 | 440.0 (M + 23) | 1 |
| 68 | 1-[6-(4-iodophenoxy) hexyl]-3-phenyl-2-imidazolidinone | 7.32-7.24 (m, 4H), 7.07 (dd, 2H), 6.76 (dd, 1H), 6.40 (d, 2H), 3.63 (t, 2H), 3.47 (dd, 2H), 3.15 (dd, 2H), 3.03 (t, 2H), 1.54-1.47 (m, 2H), 1.35-1.11 (m, 6H) | 464.3 | 465.0 | 487.0 (M + 23) | 1 |
| 69 | 1-[8-(4-chlorophenoxy) octyl]-3-(4-pyridyl)-2-imidazolidinone | 8.41 (bs, 2H), 7.49 (d, 2H), 7.19 (dd, 2H), 6.78 (dd, 2H), 3.88 (t, 2H), 3.79 (dd, 2H), 3.51 (dd, 2H), 3.28 (t, 2H), 1.76-1.71 (m, 2H), 1.57-1.52 (m, 2H), 1.41-1.33 (m, 8H) | 401.9 | 402.2 | | 1 |
| 70 | 1-phenyl-3-(6-[4-(trifluoromethyl)phenoxy] hexyl)-2-imidazolidinone | 7.52-7.45 (m, 4H), 7.27 (dd, 2H), 6.99 (dd, 1H), 6.88 (d, 2H), 3.87 (t, 2H), 3.72 (dd, 2H), 3.39 (dd, 2H), 3.25 (t, 2H), 1.78-1.73 (m, 2H), 1.57-1.37 (m, 6H) | 406.4 | 407.3 | 429.1 (M + 23) | 1 |
| 71 | 1-(5-[2-(4-bromophenoxy) ethoxy]pentyl)-3-phenyl-2-imidazolidinone | 7.46 (d, 2H), 7.29-7.21 (m, 4H), 6.93 (t, 1H), 6.72-6.68 (m, 2H), 3.98-3.93 (m, 2H), 3.67-3.60 (m, 4H), 3.44 (t, 2H), 3.30 (d, 2H), 3.18 (t, 2H), 1.59-1.47 (m, 4H), 1.36-1.33 (m, 2H) | 446.1 | 447.1 | 469.0 (M + 23) | 1 |
| 72 | 1-(5-[2-(4-bromophenoxy) ethoxy]pentyl)-3-phenyl-2-imidazolidinone | 8.41 (d, 2H), 7.60 (d, 2H), 7.44 (d, 4H), 7.34 (d, 2H), 6.92 (d, 2H), 3.99 (t, 2H), 3.85 (dd, 2H), 3.57 (dd, 2H), 3.35 (t, 2H), 1.87-1.82 (m, 2H), 1.69-1.53 (m, 4H) | 435.2 | 436.1 | | 1 |
| 73 | 1-[6-(4-(4'-chloro)biphenyl-4-yloxy)pentyl]-3-pyridin-4-yl-imidazolidin-2-one | 8.41 (d, 2H), 7.73 (d, 2H), 7.45(d, 2H), 7.44 (d, 2H), 7.35 (d, 2H), 6.92 (d, 2H), 3.99 (t, 2H), 3.89 (dd, 2H), 3.61 (dd, 2H), 3.37 (t, 2H), 1.80-1.89 (m, 2H), 1.62-1.72 (m, 2H), 1.51-1.58 (m, 2H). | 435.9 | 436.5 | 458.5 (M + 23) | 1 |
| 74 | 1-[5-(4'-methoxy-biphenyl-4-yloxy)pentyl]-3-pyridin-4-yl-imidazolidin-2-one | 8.43 (br, 2H), 7.54 (d, 2H), 7.45 (d, 2H), 7.43 (d, 2H), 6.92 (d, 4H), 3.99 (t, 2H), 3.82 (t, 2H), 3.82 (s, 3H), 3.55 (t,, 2H), 3.35 (t, 2H), 1.87-1.52 (m, 6H) | 431.5 | 432.5 | 454.3 | 1 |
| 75 | 1-[5-(biphenyl-4-yloxy)pentyl]-3-pyridin-4- | 8.43 (br, 2H), 7.54-7.47 (m, 6H), 7.39 (t, 2H), 7.29 (d, 1H), 6.93 (d, | 401.5 | 402.5 | 424.6 | 1 |

-continued

| Example (Cpd ID) | Name | NMR (CDCl$_3$, ppm) | Mass (Cald.) | M + 1 | Mass + 23 | Method |
|---|---|---|---|---|---|---|
| | yl-imidazolidin-2-one | 2H), 4.00 (t, 2H), 3.79 (t, 2H), 3.53 (t, 2H), 3.34 (t, 2H), 1.89-1.80 (m, 2H), 1.70-1.50 (m, 4H) | | | | |
| 76 | 1-[5-(4'-nitro-biphenyl-4-yloxy)pentyl]-3-pyridin-4-yl-imidazolidin-2-one | 8.43 (br, 2H), 8.24 (d, 2H), 7.65 (d, 2H), 7.54 (d, 2H), 7.47 (d, 2H), 6.96 (d, 2H), 4.00 (t, 2H), 3.80 (t, 2H), 3.54 (t, 2H), 3.34 (t, 2H), 1.88-1.83 (m, 2H), 1.68-1.53 (m, 4H) | 446.5 | 447.5 | 469.4 | 1 |

EXAMPLE 77

Test of Antiviral Activity of Various Imidazolidinone Compounds

Cells and Viruses

EV 71 isolates were obtained from Chang Gung Children's Hospitals (Taipei, Taiwan). BrCr, the prototype of EV 71, was obtained from the American Type Culture Collection (ATCC Accession No. VR 784). EV 71–2231 and EV 71–1743 were isolated from throat swabs, while EV 71–2272 was isolated from the spinal cord of a fatal case. EV 71–2086 was isolated from the skin lesion of an implicated HFMD (hand, foot, and mouth disease) patient. MRC-5 cells (ATCC Accession No. CCL-171) and vero cells (ATCC Accession No. CCL-81) were used for virus isolation and propagation.

Plaque Reduction Assay

The antiviral activity of a number of imidazolidinone compounds was determined by a standard plaque reduction assay as described in Otto et al., Antimicrobial Agents & Chemotherapy, 1985, 27:883–886.

More specifically, vero cells in monolayers were infected at a virus concentration to give approximately 50–100 plaques per monolayer in the virus control (without test compound). A compound to be tested was serially diluted and included in the agar-medium overlay. Plates were incubated at 35° C. for 96 hours. The plaques were stained with crystal violet and counted. IC$_{50}$, the concentration at which a tested compound reduced the number of plaques by 50% with respect to the untreated virus control, was then determined.

Some compounds were tested against some of the serotypes from either a panel of four human enterovirus serotypes (namely, EV 68, EV 71–2086, EV 71–2231, EV 71-BrCr, and EV 71–1743), or a panel of human coxackievirus serotypes (namely, COX-A16, -A9, -A10, -A24, -B1, -B2, -B3, -B4, -B5, and -B6), or echovirus (-9 and -29), human rhinovirus-14, HSV-1, influenza A (WSN), and influenza B (HK). The efficacy of each compound was determined in terms of IC$_{50}$, which was the concentration of the compound required to inhibit 50% of the tested virus.

All of the tested compounds (i.e., Compounds 1, 2, 17, 21, 24, 28, 33, 34, 39, 42, 47, 50, 52, 61,73, 74, 75 and 76) showed antiviral activity against enteroviruses, in particular, enterovirus 71, coxsackieviruses A9 and A24.

Other Embodiments

A number of embodiments of the invention have been described. Nevertheless, it will be understood that various modifications may be made without departing from the spirit and scope of the invention. Other aspects, advantages and modifications within the scope of this invention will be apparent to those skilled in the art to which this invention pertains. Accordingly, other embodiments are within the scope of the following claims:

What is claimed is:

1. A compound having the formula:

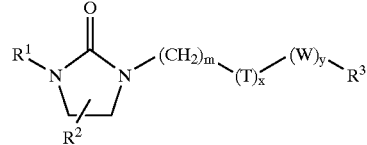

wherein each of $R^1$ and $R^3$ independently is $C_{6-12}$ aryl, $C_{6-12}$ aralkyl, or heteroaryl, optionally substituted with halogen, —OR$^4$, Cl$_{1-4}$ alkyl, C$_{1-4}$ haloalkyl, C$_{1-4}$ alkyl-OR$^4$, —CN, —NO$_2$, —C(O)R$^4$, —SR$^4$, —S(O)R$^4$, —S(O)$_2$R$^4$, —NR$^4$R$^5$, —C(O)OR$^4$, —C(O)N R$^4$R$^5$, —NO$_2$, —O(O)CR$^4$, —NR$^4$(O)CR$^5$, —NR$^4$C(O)OR$^5$, —NR$^4$C(O)NR$^5$R$^6$, or R$^7$, provided that if R$^1$ is heteroaryl, the heteroaryl forms a C—N bond with the imidazolidinone ring; in which each of R$^4$, R$^5$, and R$^6$, independently, is H or C$_{1-4}$ alkyl; and R$^7$ is C$_{6-12}$ aryl, C$_{6-12}$ aralkyl, or heteroaryl, optionally substituted with halogen, C$_{1-4}$ alkyl, C$_{1-4}$ haloalkyl, —OR$^4$, —NO$_2$, —C(O)OR$^4$, —CN, —NR$^4$R$^5$, or —NR$^4$C(O)OR$^5$;

$R^2$ is H, C$_{1-5}$ alkyl, C$_{1-5}$ haloalkyl, C$_{6-12}$ aryl, C$_{6-12}$ aralkyl, or heteroaryl, optionally substituted with halogen, —OR$^4$, C$_{1-4}$ alkyl, C$_{1-4}$ haloalkyl, C$_{1-4}$ alkyl-OR$^4$, —CN, —C(O)R$^4$, —SR$^4$, —S(O)R$^4$, —S(O)$_2$R$^4$, —NR$^4$R$^5$, —C(O)OR$^4$, —C(O)NR$^4$R$^5$, —NO$_2$, —O(O)CR$^4$, —NR$^4$(O)CR$^5$, —NR$^4$C(O)OR$^5$, or —NR$^4$C(O)NR$^5$R$^6$; in which R$^4$, R$^5$, R$^6$, and R$^7$ are defined as above;

T is NH or O;

W is —CH$_2$—O—, —(CH$_2$)$_2$—O—, —(CH$_2$)$_3$—O—, or —(CH$_2$)$_4$—O—;

m is 4, 5, 6, 7 or 8; and each of x and y independently is 0 or 1, provided that at least one of x and y is 1.

2. The compound of claim 1, wherein each of R$^1$ and R$^3$, independently, is C$_{6-12}$ aryl, C$_{6-12}$ aralkyl, or heteroaryl, optionally substituted with halogen, —OR$^4$, C$_{1-4}$ alkyl, C$_{1-4}$ haloalkyl, C$_{1-4}$ alkyl-OR$^4$, —NO$_2$, —CN, —SR$^4$, —NR$^4$R$^5$, —NR$^4$C(O)NR$^5$R$^6$, or R$^7$; and R$^7$ is C$_{6-12}$ aryl or heteroaryl, optionally substituted with C$_{1-4}$ haloalkyl, halogen, —OR$^4$, or —NO$_2$.

3. The compound of claim 2, wherein each of R$^1$ and R$^3$, independently, is pyridinyl, phenyl, or thiazolyl, optionally substituted with halogen, —OR$^4$, C$_{1-4}$ alkyl, C$_{1-4}$ haloalkyl, C$_{1-4}$ alkyl-OR$^4$, —NO$_2$, —CN, —SR$^4$, —NR$^4$R$^5$, —NR$^4$C (O)NR$^5$R$^6$, or R$^7$; and R$^7$ is C$_{6-12}$ aryl or heteroaryl, optionally substituted with C$_{1-4}$ haloalkyl, halogen, —OR$^4$, or —NO$_2$.

4. The compound of claim 2, wherein $R^2$ is H, $C_{1-5}$ alkyl, $C_{1-5}$ haloalkyl, $C_{6-12}$ aryl, $C_{6-12}$ aralkyl, or heteroaryl, optionally substituted with halogen, —$OR^4$, $C_{1-4}$ alkyl, $C_{1-4}$ haloalkyl, $C_{1-4}$ alkyl-$OR^4$, —CN, —$SR^4$, —$NR^4R^5$, or —C(O)$NR^4R^5$.

5. The compound of claim 4, wherein each of $R^1$ and $R^3$, independently, is pyridinyl, phenyl, or thiazolyl, optionally substituted with halogen, —$OR^4$, $C_{1-4}$ alkyl, $C_{1-4}$ haloalkyl, $C_{1-4}$ alkyl-$OR^4$, —$NO_2$, —CN, —$SR^4$, —$NR^4R^5$, —$NR^4C(O)NR^5R^6$, or $R^7$; and $R^7$ is $C_{6-12}$ aryl or heteroaryl, optionally substituted with $C_{1-4}$ haloalkyl, halogen, —$OR^4$, or —$NO_2$.

6. The compound of claim 4, wherein x is 1, and T is O.

7. The compound of claim 6, wherein each of $R^1$ and $R^3$, independently, is pyridinyl, phenyl, or thiazolyl, optionally substituted with halogen, —$OR^4$, $C_{1-4}$ alkyl, $C_{1-4}$ haloalkyl, $C_{1-4}$ alkyl-$OR^4$, —$NO_2$, —CN, —$SR^4$, —$NR^4R^5$, —$NR^4C(O)NR^5R^6$, or $R^7$; and $R^7$ is $C_{6-12}$ aryl or heteroaryl, optionally substituted with $C_{1-4}$ haloalkyl, halogen, —$OR^4$, or —$NO_2$.

8. The compound of claim 2, wherein x is 1, and T is O.

9. The compound of claim 1, wherein $R^2$ is H, $C_{1-5}$ alkyl, $C_{1-5}$ haloalkyl, $C_{6-12}$ aryl, $C_{6-12}$ aralkyl, or heteroaryl, optionally substituted with halogen, —$OR^4$, $C_{1-4}$ alkyl, $C_{1-4}$ haloalkyl, $C_{1-4}$ alkyl-$OR^4$, —CN, —$SR^4$, —$NR^4R^5$, or —C(O)$NR^4R^5$.

10. The compound of claim 9, wherein x is 1, and T is O.

11. The compound of claim 1, wherein x is 1, and T is O.

12. The compound of claim 1, wherein y is 1, and W is —$(CH_2)_2$—O— or —$(CH_2)_3$—O—.

13. The compound of claim 12, wherein x is 1, and T is O.

14. The compound of claim 13, wherein each of $R^1$ and $R^3$, independently, is $C_{6-12}$ aryl, $C_{6-12}$ aralkyl, or heteroaryl, optionally substituted with halogen, —$OR^4$, $C_{1-4}$ alkyl, $C_{1-4}$ haloalkyl, $C_{1-4}$ alkyl-$OR^4$, —$NO_2$, —CN, —$SR^4$, —$NR^4R^5$, —$NR^4C(O)NR^5R^6$, or $R^7$; and $R^7$ is $C_{6-12}$ aryl or heteroaryl, optionally substituted with $C_{1-4}$ haloalkyl, halogen, —$OR^4$, or —$NO_2$.

15. The compound of claim 13, wherein $R^2$ is H, $C_{1-5}$ alkyl, $C_{1-5}$ haloalkyl, $C_{6-12}$ aryl, $C_{6-12}$ aralkyl, or heteroaryl, optionally substituted with halogen, —$OR^4$, $C_{1-4}$ alkyl, $C_{1-4}$ haloalkyl, $C_{1-4}$ alkyl-$OR^4$, —CN, —$SR^4$, —$NR^4R^5$, or —C(O)$NR^4R^5$.

16. The compound of claim 15, wherein each of $R^1$ and $R^3$, independently, is $C_{6-12}$ aryl, $C_{6-12}$ aralkyl, or heteroaryl, optionally substituted with halogen, —$OR^4$, $C_{1-4}$ alkyl, $C_{1-4}$ haloalkyl, $C_{1-4}$ alkyl-$OR^4$, —$NO_2$, —CN, —$SR^4$, —$NR^4R^5$, —$NR^4C(O)NR^5R^6$, or $R^7$; and $R^7$ is $C_{6-12}$ aryl or heteroaryl, optionally substituted with $C_{1-4}$ haloalkyl, halogen, —$OR^4$, or —$NO_2$.

17. The compound of claim 12, wherein each of $R^1$ and $R^3$, independently, is $C_{6-12}$ aryl, $C_{6-12}$ aralkyl, or heteroaryl, optionally substituted with halogen, —$OR^4$, $C_{1-4}$ alkyl, $C_{1-4}$ haloalkyl, $C_{1-4}$ alkyl-$OR^4$, —$NO_2$, —CN, —$SR^4$, —$NR^4R^5$, —$NR^4C(O)NR^5R^6$, or $R^7$; and $R^7$ is $C_{6-12}$ aryl or heteroaryl, optionally substituted with $C_{1-4}$ haloalkyl, halogen, —$OR^4$, or —$NO_2$.

18. The compound of claim 17, wherein $R^2$ is H, $C_{1-5}$ alkyl, $C_{1-5}$ haloalkyl, $C_{6-12}$ aryl, $C_{6-12}$ aralkyl, or heteroaryl, optionally substituted with halogen, —$OR^4$, $C_{1-4}$ alkyl, $C_{1-4}$ haloalkyl, $C_{1-4}$ alkyl-$OR^4$, —CN, —$SR^4$, —$NR^4R^5$, or —C(O)$NR^4R^5$.

19. The compound of claim 17, wherein x is 1, and T is O.

20. The compound of claim 19, wherein $R^2$ is H, $C_{1-5}$ alkyl, $C_{1-5}$ haloalkyl, $C_{6-12}$ aryl, $C_{6-12}$ aralkyl, or heteroaryl, optionally substituted with halogen, —$OR^4$, $C_{1-4}$ alkyl, $C_{1-4}$ haloalkyl, $C_{1-4}$ alkyl-$OR^4$, —CN, —$SR^4$, —$NR^4R^5$, or —C(O)$NR^4R^5$.

21. The compound of claim 17, wherein each of $R^1$ and $R^3$, independently, is pyridinyl, phenyl, or thiazolyl, optionally substituted with halogen, —$OR^4$, $C_{1-4}$ alkyl, $C_{1-4}$ haloalkyl, $C_{1-4}$ alkyl-$OR^4$, —$NO_2$, —CN, —$SR^4$, —$NR^4R^5$, —$NR^4C(O)NR^5R^6$, or $R^7$; and $R^7$ is $C_{6-12}$ aryl or heteroaryl, optionally substituted with $C_{1-4}$ haloalkyl, halogen, —$OR^4$, or —$NO_2$.

22. The compound of claim 12, wherein $R^2$ is H, $C_{1-5}$ alkyl, $C_{1-5}$ haloalkyl, $C_{6-12}$ aryl, $C_{6-12}$ aralkyl, or heteroaryl, optionally substituted with halogen, —$OR^4$, $C_{1-4}$ alkyl, $C_{1-4}$ haloalkyl, $C_{1-4}$ alkyl-$OR^4$, —CN, —$SR^4$, —$NR^4R^5$, or —C(O)$NR^4R^5$.

23. The compound of claim 12, wherein the compound is

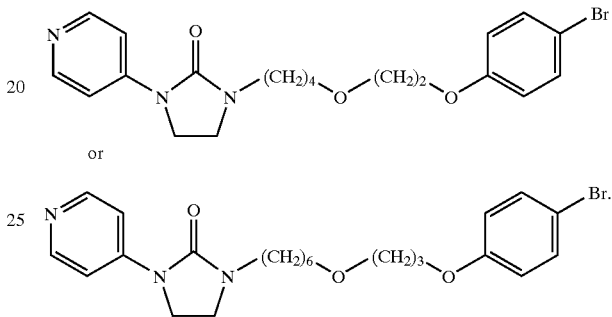

24. The compound of claim 1, wherein y is 0.

25. The compound of claim 24, wherein each of $R^1$ and $R^3$, independently, is $C_{6-12}$ aryl, $C_{6-12}$ aralkyl, or heteroaryl, optionally substituted with halogen, —$OR^4$, $C_{1-4}$ alkyl, $C_{1-4}$ haloalkyl, $C_{1-4}$ alkyl-$OR^4$, —$NO_2$, —CN, —$SR^4$, —$NR^4R^5$, —$NR^4C(O)NR^5R^6$, or $R^7$; and $R^7$ is $C_{6-12}$ aryl or heteroaryl, optionally substituted with $C_{1-4}$ haloalkyl, halogen, —$OR^4$, or —$NO_2$.

26. The compound of claim 24, wherein $R^2$ is H, $C_{1-5}$ alkyl, $C_{1-5}$haloalkyl, $C_{6-12}$ aryl, $C_{6-12}$ aralkyl, or heteroaryl, optionally substituted with halogen, —$OR^4$, $C_{1-4}$ alkyl, $C_{1-4}$ haloalkyl, $C_{1-4}$ alkyl-$OR^4$, —CN, —$SR^4$, —$NR^4R^5$, or —C(O)$NR^4R^5$.

27. The compound of claim 26, wherein each of $R^1$ and $R^3$, independently, is $C_{6-12}$ aryl, $C_{6-12}$ aralkyl, or heteroaryl, optionally substituted with halogen, —$OR^4$, $C_{1-4}$ alkyl, $C_{1-4}$ haloalkyl, $C_{1-4}$ alkyl-$OR^4$, —$NO_2$, —CN, —$SR^4$, —$NR^4R^5$, —$NR^4C(O)NR^5R^6$, or $R^7$; and $R^7$ is $C_{6-12}$ aryl or heteroaryl, optionally substituted with $C_{1-4}$ haloalkyl, halogen, —$OR^4$, or —$NO_2$.

28. The compound of claim 27, wherein each of $R^1$ and $R^3$, independently, is pyridinyl, phenyl, or thiazolyl, optionally substituted with halogen, —$OR^4$, $C_{1-4}$ alkyl, $C_{1-4}$ haloalkyl, $C_{1-4}$ alkyl-$OR^4$, —$NO_2$, —CN, —$SR^4$, —$NR^4R^5$, —$NR^4C(O)NR^5R^6$, or $R^7$; and $R^7$ is $C_{6-12}$ aryl or heteroaryl, optionally substituted with $C_{1-4}$ haloalkyl, halogen, —$OR^4$, or —$NO_2$.

29. The compound of claim 24, wherein x is 1, and T is O.

30. The compound of claim 29, wherein each of $R^1$ and $R^3$, independently, is $C_{6-12}$ aryl, $C_{6-12}$ aralkyl, or heteroaryl, optionally substituted with halogen, —$OR^4$, $C_{1-4}$ alkyl, $C_{1-4}$ haloalkyl, $C_{1-4}$ alkyl-$OR^4$, —$CO_2$, —CN, —$SR^4$, —$NR^4R^5$, —$NR^4C(O)NR^5R^6$, or $R^7$; and $R^7$ is $C_{6-12}$ aryl or heteroaryl, optionally substituted with $C_{1-4}$ haloalkyl, halogen, —$OR^4$, or —$NO_2$.

31. The compound of claim 29, wherein $R^2$ is H, $C_{1-5}$ alkyl, $C_{1-5}$ haloalkyl, $C_{6-12}$ aryl, $C_{6-12}$ aralkyl, or heteroaryl, optionally substituted with halogen, —OR$^4$, $C_{1-4}$ alkyl, $C_{1-4}$ haloalkyl, $C_{1-4}$ alkyl-OR$^4$, —CN, —SR$^4$, —NR$^4$R$^5$, or —C(O)NR$^4$R$^5$.

32. The compound of claim 31, wherein each of R$^1$ and R$^3$, independently, is $C_{6-12}$ aryl, $C_{6-12}$ aralkyl, or heteroaryl, optionally substituted with halogen, —OR$^4$, $C_{1-4}$ alkyl, $C_{1-4}$ haloalkyl, $C_{1-4}$ alkyl-OR$^4$, —NO$_2$, —CN, —SR$^4$, —NR$^4$R$^5$, —NR$^4$C(O)NR$^5$R$^6$, or R$^7$; and R$^7$ is $C_{6-12}$ aryl or heteroaryl, optionally substituted with $C_{1-4}$ haloalkyl, halogen, —OR$^4$, or —NO$_2$.

33. The compound of claim 24, wherein the compound is

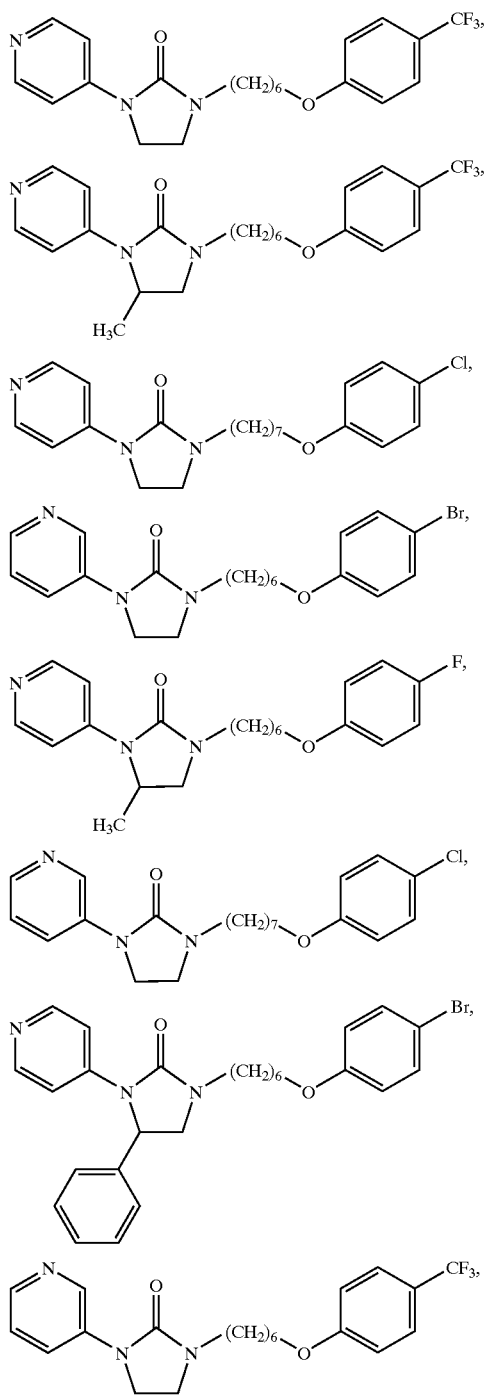

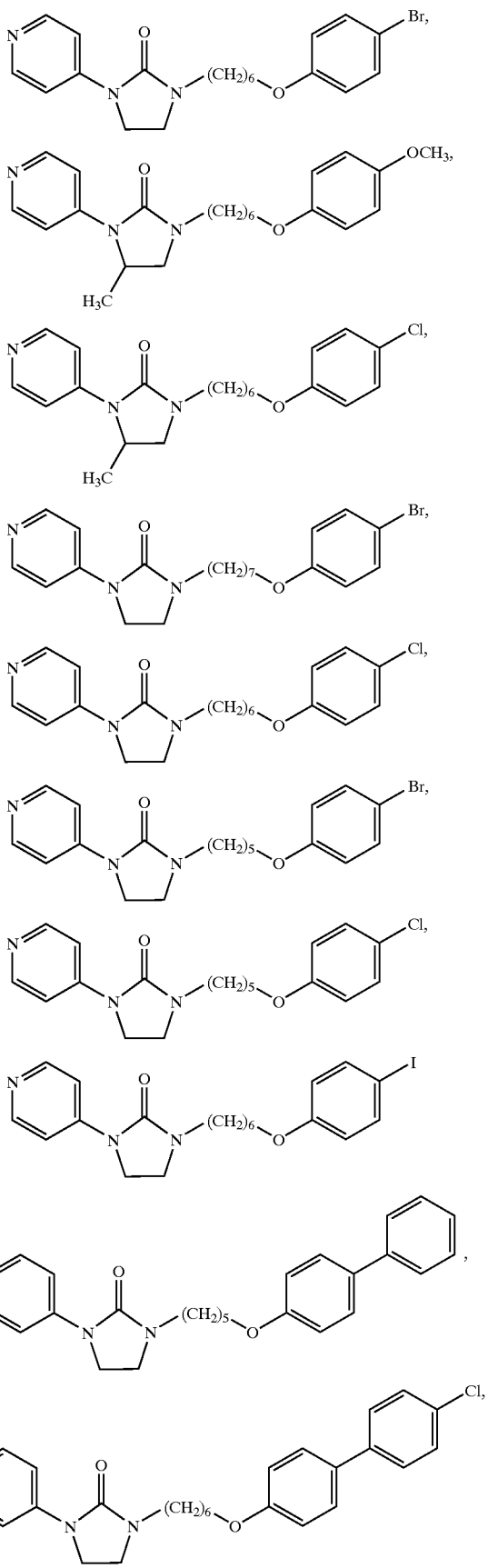

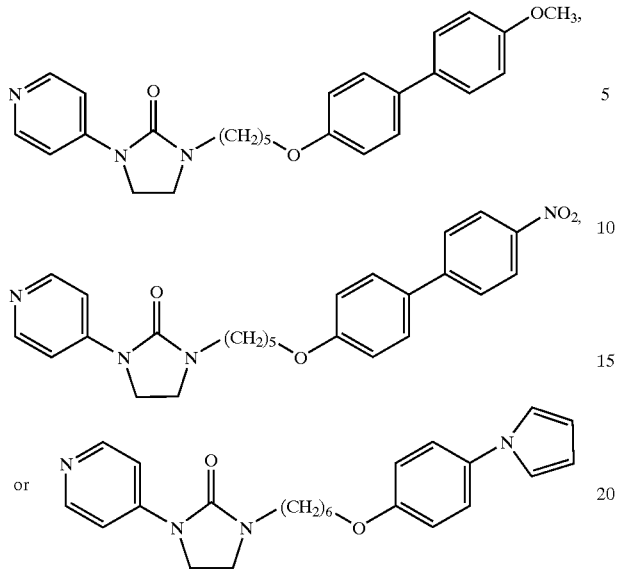

34. A method of treating infection by an enterovirus, comprising administering to a subject in need thereof an effective amount of a compound having the formula:

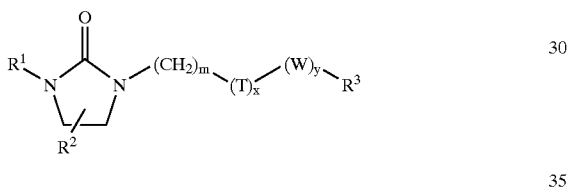

wherein
each of $R^1$ and $R^3$ independently is $C_{6-12}$ aryl, $C_{6-12}$ aralkyl, or heteroaryl, optionally substituted with halogen, —$OR^4$, $C_{1-4}$ alkyl, $C_{1-4}$ haloalkyl, $C_{1-4}$ alkyl-$OR^4$, —$NO_2$, —CN, —$C(O)R^4$, —$SR^4$, —$S(O)R^4$, —$S(O)_2R^4$, —$NR^4R^5$, —$C(O)OR^4$, $C(O)NR^4R^5$, —$NO_2$, —$O(O)CR^4$, —$NR^4(O)CR^5$, —$NR^4C(O)OR^1$, —$NR^4C(O)NR^5R^6$, or $R^7$, provided that if $R^1$ is heteroaryl, the heteroaryl forms a C—N bond with the imidazolidinone ring; in which each of $R^4$, $R^5$, and $R^6$, independently, is H or $C_{1-4}$ alkyl; and $R^7$ is $C_{6-12}$ aryl, $C_{6-12}$ aralkyl, or heteroaryl, optionally substituted with halogen, $C_{1-4}$ alkyl, $C_{1-4}$ haloalkyl, —$OR^4$, —$NO_2$, —$C(O)OR^4$, —CN, —$NR^4R^5$, or —$NR^4C(O)OR^5$;
$R^2$ is H, $C_{1-5}$ alkyl, $C_{1-5}$ haloalkyl, $C_{6-12}$ aryl, $C_{6-12}$ aralkyl, or heteroaryl, optionally substituted with halogen, —$OR^4$, $C_{1-4}$ alkyl, $C_{1-4}$ haloalkyl, $C_{1-4}$ alkyl-$OR^4$, —CN, —$C(O)R^4$, —$SR^4$, —$S(O)R^4$, —$S(O)_2R^4$, —$NR^4R^5$, —$C(O)OR^4$, —$C(O)NR^4R^5$, —$NO_2$, —$O(O)CR^4$, —$NR^4(O)CR^5$, —$NR^4C(O)OR^5$, or —$NR^4C(O)NR^5R^6$; in which $R^4$, $R^5$, $R^6$, and $R^7$ are defined as above;
T is NH or O;
W is —$CH_2$—O—, —$(CH_2)_2$—O—, —$(CH_2)_3$—O—, or —$(CH_2)_4$—O—;
m is 4, 5, 6, 7 or 8; and
each of x and y independently is 0 or 1, provided that at least one of x and y is 1.

35. The method of claim 34, wherein x is 1, and T is O.
36. The method of claim 34, wherein y is 1, and W is —$(CH_2)_2$—O— or —$(CH_2)_3$—O—.
37. The method of claim 34, wherein y is 0.
38. The method of claim 34, wherein the compound is

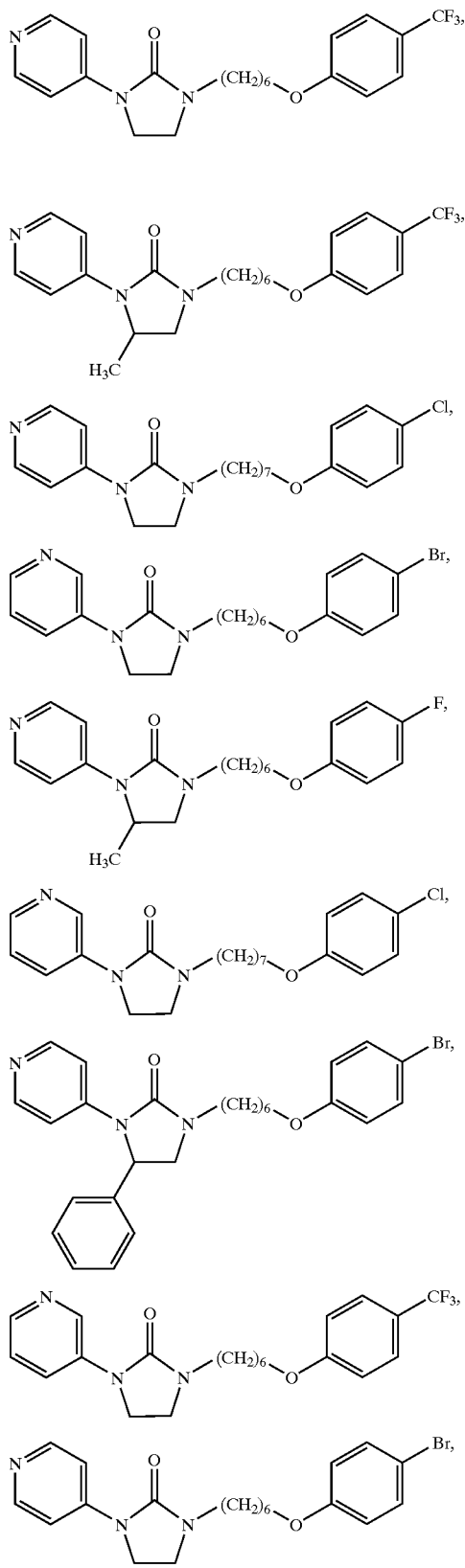

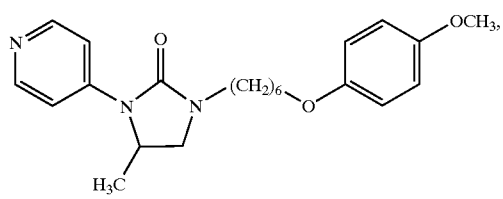
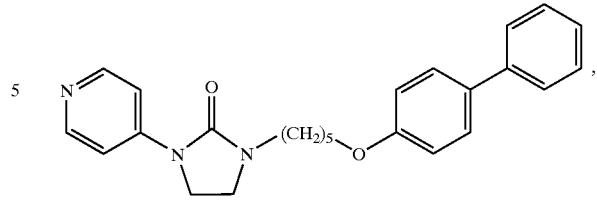
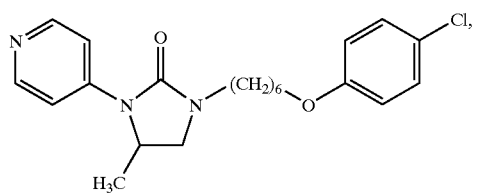
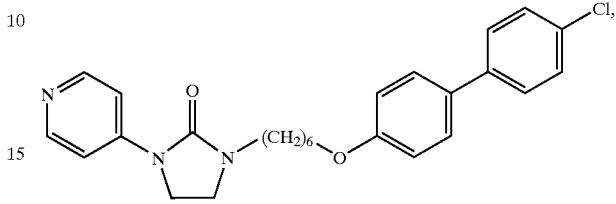
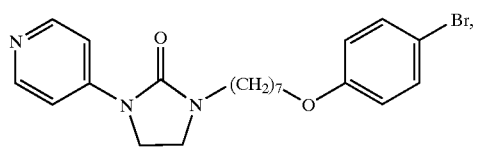
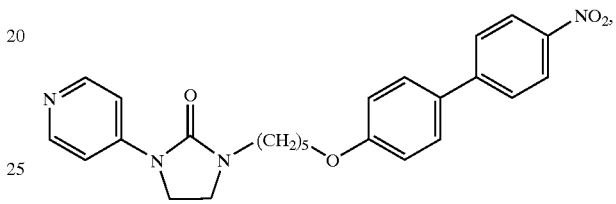
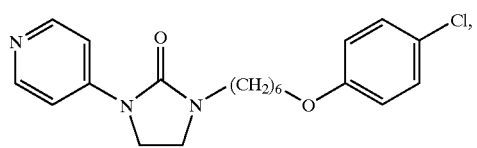
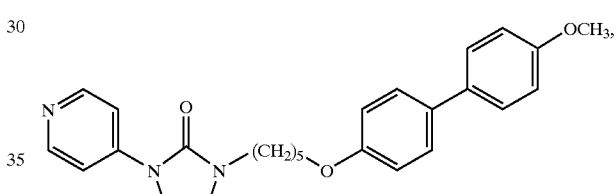
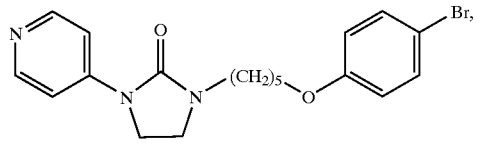
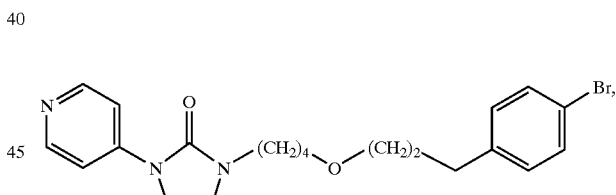
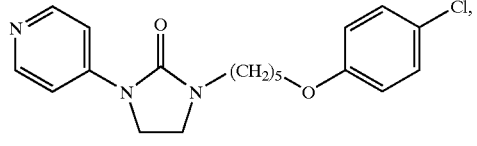
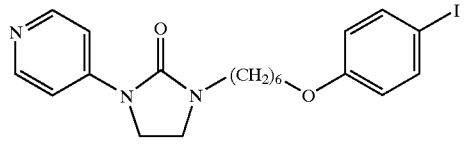
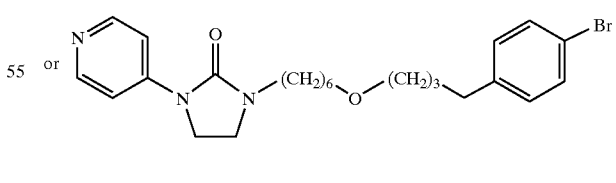
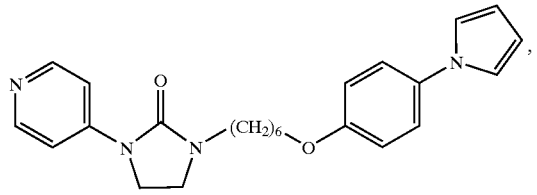
* * * * *